United States Patent [19]
Johnson et al.

[11] Patent Number: 6,166,008
[45] Date of Patent: Dec. 26, 2000

[54] TREATMENT OF SCHIZOPHRENIA WITH AMPAKINES AND NEUROLEPTICS

[75] Inventors: Steven A. Johnson, Costa Mesa; Gary S. Lynch, Irvine; Gary A. Rogers, Santa Barbara, all of Calif.

[73] Assignees: Cortex Pharmaceuticals, Inc., Irvine, Calif.; The Regents of the University of California, Oakland, Calif.

[21] Appl. No.: 09/179,341

[22] Filed: Oct. 26, 1998

Related U.S. Application Data

[60] Provisional application No. 60/063,627, Oct. 27, 1997.

[51] Int. Cl.[7] .................................................. A61K 31/535
[52] U.S. Cl. ..................... 514/223.2; 514/229.2; 514/249; 514/321; 514/338; 514/354; 514/410; 514/411; 514/423
[58] Field of Search ............................. 514/223.2, 229.2, 514/249, 321, 338, 354, 410, 411, 423

[56] References Cited

FOREIGN PATENT DOCUMENTS

WO 97/07799 A1  3/1997  WIPO .

OTHER PUBLICATIONS

Vanover of the abstract to, "Effects of AMPA receptor positive modulators on amphetamine– and dizocilpine–induced locomotion", European Journal of Pharmacology, vol. 332, Issue: 2, Aug. 6, 1997.

*Primary Examiner*—Dwayne C. Jones
*Attorney, Agent, or Firm*—Townsend and Townsend and Crew LLP

[57] ABSTRACT

This invention relates to treatment of schizophrenia and related psychotic disorders, including enhancement of receptor functioning in synapses in brain networks responsible for higher order behaviors. In a particular aspect, the invention relates to methods for the use of AMPA receptor up-modulators in conjunction with antipsychotics for the treatment of schizophrenia. Kits containing the compositions in appropriate form for administration are also provided.

26 Claims, 4 Drawing Sheets

TREATMENT OF SCHIZOPHRENIA WITH AMPAKINES AND NEUROLEPTICS

The present invention claims priority from U.S. provisional application Ser. No. 60/063,627, filed on Oct. 27, 1997, hereby incorporated by reference.

BACKGROUND OF THE INVENTION

This invention relates to treatment of schizophrenia and other psychotic disorders. This invention especially relates to treatment of schizophrenia and other psychotic disorders by enhancement of receptor functioning in synapses in brain networks responsible for higher order behaviors. In particular, the invention provides methods for the use of AMPA receptor up-modulators in conjunction with antipsychotics for the treatment of schizophrenia.

The release of glutamate at synapses at many sites in mammalian forebrain stimulates two classes of postsynaptic receptors. These classes are usually referred to as α-amino-3-hydroxy-5-methyl-4-isoxazole propionic acid (AMPA)/quisqualate and N-methyl-D-aspartic acid (NMDA) receptors. AMPA/quisqualate receptors mediate a voltage-independent fast excitatory post-synaptic current (the fast epsc) whereas NMDA receptors generate a voltage-dependent, slow excitatory current. Studies carried out in slices of hippocampus or cortex indicate that the AMPA receptor-mediated fast epsc is by far the dominant component at most glutamatergic synapses under most circumstances.

AMPA receptors are not evenly distributed across the brain but instead are largely restricted to telencephalon and cerebellum. These receptors are found in high concentrations in the superficial layers of neocortex, in each of the major synaptic zones of hippocampus, and in the striatal complex, as reported by Monaghan et al., in *Brain Research* 324:160–164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

Schizophrenia is a chronic disease that is characterized by positive (hallucinations, delusions), negative (social withdrawal, flattened affect) and cognitive (formal thought disorder, executive memory dysfunction) symptoms. The dopamine hypothesis, that schizophrenia stems from excessive midbrain dopamine transmission, originated from studies with neuroleptics that revealed correlations between clinical efficacy, effects on dopamine metabolism (Carlsson & Lindqvist, *Acta Pharmacol. Toxicol.* 20:140–144, 1967) and binding to dopamine receptors (Creese et al., *Science* 192:481–482, 1976). In addition, drugs that increase synaptic dopamine concentration, (e.g., amphetamines) produce aberrant, stereotyped behavior in animals (WT McKinney, in SC Shultz and CA Tamminga (eds) *Schizophrenia: Scientific Progress*. Oxford University Press, New York, pp 141–154, 1989) and schizophrenia-like symptoms in humans (Snyder, *Am. J Psychol.* 130:61–67, 1976).

However, accumulating evidence suggests that schizophrenia may also be caused by reduced neocortical glutamatergic function. In vivo imaging studies have shown reduced metabolic activity (Andreasen et al., *Lancet* 349:1730–1734, 1997; Weinberger and Berman, *Philos. Trans. R Soc. Lond. B Biol. Sci* 351:1495–1503, 1996) in frontal and temporal cortices that are rich in glutamatergic (excitatory) synapses. Histopathologic studies have documented cytoarchitectural abnormalities (reviewed in Weinberger and Lipska, *Schizophrenia Res.* 16:87–110, 1995), as well as reduced neuron or synapse densities and reduced AMPA receptor (AMPA-R) densities in these same areas in post-mortem schizophrenic brain (Eastwood et. al., *Biol. Psychiatry* 41:636–643, 1997), including hippocampus (Breese et al., *Brain Res.* 674:82–90, 1995). This evidence is further supported by recent molecular studies that showed decreased AMPA-R subunit mRNA prevalence in neocortex (Eastwood et al., *Mol. Brain Res.* 29:211–223, 1995) and hippocampus of schizophrenic brains (Eastwood et. al., *Mol. Brain Res.* 44:92–98, 1997). Neurochemical studies have found reduced glutamate concentrations in cerebrospinal fluid (Kim et al., *Neuroscience Letters* 20:379–382, 1980) and lower glutamate and aspartate levels in prefrontal and temporolimbic areas (Tsai et al., *Arch. Gen. Psychiatry* 52:829–836, 1995). Finally, phencyclidine (PCP), ketamine and other use-dependent antagonists at NMDA-R produce aberrant behavior in animals (Freed et al., *Psychopharmacology* 71: 291–297, 1980), exacerbate symptoms in patients (Lahti et al., *Neuropsychopharmacology* 13:9–19, 1995), and produce a range of psychotic symptoms in volunteers that can accurately mimic symptoms of schizophrenic patients (Krystal et al., *Arch. Gen. Psychiatry* 51:199–214, 1994). Thus, significant recent evidence supports the 'hypofrontality' hypothesis of reduced excitatory tone in frontotemporal cortices of the schizophrenic brain.

For the reasons set forth above, drugs that enhance the functioning of AMPA receptors have significant benefits for the treatment of schizophrenia. See, e.g., U.S. application Ser. No. 08/521,022. Such drugs should also ameliorate the cognitive symptoms that are not addressed by currently-used antipsychotics. Experimental studies, such as those reported by Arai and Lynch, *Brain Research*, 598:173–184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning. Compounds that enhance the functioning of the AMPA form of glutamate receptors facilitate the induction of LTP and the acquisition of learned tasks as measured by a number of paradigms: Granger et al., *Synapse* 15:326–329 (1993); Staubli et al., *PNAS* 91:777–781 (1994); Arai et al., *Brain Res.* 638:343–346 (1994); Staubli et al., *PNAS* 91:11158–11162 (1994); Shors et al., *Neurosci. Let.* 186:153–156 (1995); Larson et al., *J. Neurosci.* 15:8023–8030 (1995); Granger et al., *Synapse* 22:332–337 (1996); Arai, et al., *JPET* 278:627–638 (1996); Lynch et al., *Internat. Clin. Psychopharm.* 11:13–19 (1996); Lynch et al., *Exp. Neurology* 145:89–92 (1997); Ingvar et al., *Exp. Neurology* 146:553–559 (1997); and Lynch and Rogers, WO 94/02475 (PCT/US93/06916).

There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, *Neuroscience* 49:1–6 (1992). A possible prototype for a compound that selectively facilitates the AMPA receptor was disclosed by Ito et al., *J. Physiol.* 424:533–543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials. See, for example, Staubli et al., in *Psychobiology* 18:377–381 (1990) and Xiao et al., *Hippocampus* 1:373–380 (1991). Aniracetam has also been found to have an extremely rapid onset and washout, and can be applied repeatedly with no apparent lasting effects; these are valuable traits for behaviorally-relevant drugs. Unfortunately, the peripheral administration of aniracetam is not likely to influence brain receptors. The drug works only at high concentrations (~1.0 mM) and Guenzi and Zanetti, *J. Chromatogr.* 530:397–406 (1990) report that about 80% of the drug is converted to anisoyl-GABA following peripheral administration in humans. The metabolite, anisoyl-GABA, has been found to have only weak aniracetam-like effects.

SUMMARY OF THE INVENTION

The present invention is based on the discovery that synaptic responses mediated by AMPA receptors are increased by administration of a novel class of compounds known as Ampakines. In particular, the present invention is based on the discovery that Ampakines are useful to treat Schizophrenia or Schizophreniform Disorder or Schizoaffective Disorder or Delusional Disorder or Brief Psychotic Disorder or Psychotic Disorder Due to a General Medical Condition or Psychotic Disorder Not Otherwise Specified. It is now apparent that compounds of the Ampakine family can interact with neuroleptics/antipsychotics in reversing behavior in animals in ways that predict success in treating subjects diagnosed as suffering from schizophrenia or related disorders. The interaction with the antipsychotics in these animal models of schizophrenia is not only additive, but, surprisingly synergistic. Thus, schizophrenia is treatable by compounds that enhance glutamatergic neural transmission.

The present invention comprises methods, compositions and kits for treating schizophrenia in a subject in need thereof by up-modulating the stimulatory effect of natural ligands of α-amino-3-hydroxy-5-methyl-isoxazole-4-propionic acid ("AMPA") receptors. A number of glutamatergic up-modulators may be used in the present invention; for example, 7-chloro-3-methyl-3-4-dihydro-2H-1,2,4 benzothiadiazine S,S, dioxide.

In one embodiment, the invention comprises administering to a subject an effective amount of a compound having the following formula (with ring vertices numbered as shown):

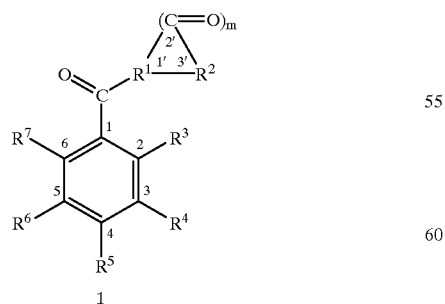

1 in which:
$R^1$ is a member selected from the group consisting of N and CH;

m is 0 or 1;
$R^2$ is a member selected from the group consisting of $(CR^8{}_2)_{n-m}$ and $C_{n-m}R^8{}_{2(n-m)-2}$, in which n is 4, 5, 6, or 7, the $R^8$'s in any single compound being the same or different, each $R^8$ being a member selected from the group consisting of H and $C_1$–$C_6$ alkyl, or one $R^8$ being combined with either $R^3$ or $R^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of $CH_2$, $CH_2$—$CH_2$, CH=CH, O, NH, N($C_1$–$C_6$ alkyl), N=CH, N=C ($C_1$–$C_6$ alkyl), C(O), O—C(O), C(O)—O, CH(OH), NH—C(O), and N($C_1$–$C_6$ alkyl)—C(O);
$R^3$, when not combined with any $R^8$, is a member selected from the group consisting of H, $C_1$–$C_6$ alkyl, and $C_1$–$C_6$ alkoxy;
$R^4$ is either combined with $R^5$ or is a member selected from the group consisting of H, OH, and $C_1$–$C_6$ alkoxy;
$R^5$ is either combined with $R^4$ or is a member selected from the group consisting of H, OH, $C_1$–$C_6$ alkoxy, amino, mono($C_1$–$C_6$ alkyl)amino, di($C_1$–$C_6$ alkyl) amino, and $CH_2OR^9$, in which $R^9$ is a member selected from the group consisting of H, $C_1$–$C_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of $C_1$–$C_3$ alkyl, $C_1$–$C_3$ alkoxy, hydroxy, halo, amino, alkylamino, dialkylamino, and methylenedioxy;
$R^6$ is either H or $CH_2OR^9$;
$R^4$ and $R^5$, when combined, form a member selected from the group consisting of

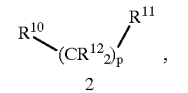

2

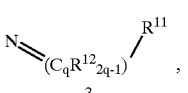

3

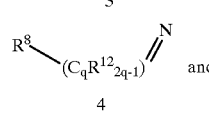

and

4

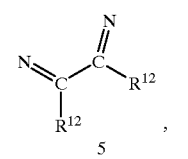

5 in which:
$R^{10}$ is a member selected from the group consisting of O, NH and N($C_1$–$C_6$ alkyl);
$R^{11}$ is a member selected from the group consisting of O, NH and N($C_1$–$C_6$ alkyl);
$R^{12}$ is a member selected from the group consisting of H and $C_1$–$C_6$ alkyl, and when two or more $R^{12}$'s are present in a single compound, such $R^{12}$'s are the same or different;
p is 1, 2, or 3; and
q is 1 or 2; and $R^7$, when not combined with any $R^8$, is a member selected from the group consisting of H, $C_1$–$C_6$ alkyl, and $C_1$–$C_6$ alkoxy.

A preferred embodiment CX516, has the following structure:

In another embodiment, the Ampakine has the following structure:

in which:

$R^1$ is oxygen or sulfur;

$R^2$ and $R^3$ are independently selected from the group consisting of —N=, —CR=, and —CX=;

M is =N or =CR$^4$—, wherein $R^4$ and $R^8$ are independently R or together form a single linking moiety linking M to the ring vertex 2', the linking moiety being selected from the group consisting of a single bond, —CR$_2$—, —CR=CR—, —C(O)—, —O—, —S(O)$_y$—, —NR—, and —N=;

$R^5$ and $R^7$ are independently selected from the group consisting of —(C$_2$)$_n$—, —C(O)—, —CR=CR—, —CR=CX—, —C(RX)—, —CX$_2$—, —S—, and —O—; and $R^6$ is selected from the group consisting of —(CR$_2$)$_m$—, —C(O)—, —CR=CR—, —C(RX)—, —CR$_2$—, —S—, and —O—;

wherein

X is —Br, —Cl, —F, —CN, —NO$_2$, —OR, —SR, —NR$_2$, —C(O)R—, —CO$_2$R, or —CONR$_2$; and R is hydrogen, $C_1$–$C_6$ branched or unbranched alkyl, which may be unsubstituted or substituted with one or more functionalities defined above as X, or aryl, which may be unsubstituted or substituted with one or more functionalities defined above as X;

m and p are independently 0 or 1;

n and y are independently 0, 1 or 2.

Preferred embodiments include:

Typical Ampakine dosages for systemic administration can range from milligrams to decigrams per kg weight of subject per administration. Preferably, the glutamatergic drug used has a rapid onset.

The Ampakine compounds of the invention are preferably administered together with a typical or atypical antipsychotic drug. Typical antipsychotics include: haloperidol, fluphenazine, perphenazine, chlorpromazine, molindone, pimozide, trifluoperazine and thioridazine, and others. Atypical antipsychotics include: clozapine, risperidone, olanzapine, sertindole, M100907, ziprasidone, seroquel, zotepine, amisulpride, iloperidone and others. The antipsychotic drug may be administered at a subtherapeutic doses, i.e., at a lower dose than the dosage that is typically used for treatments with the antipsychotic drugs alone.

Kits containing the compositions in the form of tablets or ampules or other suitable packaging means, formulated for controlled dosage administration, are also provided.

BRIEF DESCRIPTION OF THE DRAWINGS

In FIG. 1, behavioral activity was monitored with a computerized photobeam system as described in Example 2. Each point represents the mean cummulative rearing score for the previous 10 minute interval. There was a large induction of rearing activity by 2.0 mg/kg methamphetamine (i.p.), compared to saline vehicle. Clozapine (1.0 mg/kg) had no significant effect on methamphetamine-induced stereotypic rearing. CX516 (10 mg/kg) produced a small, but statistically insignificant antagonism of methamphetamine-induced rearing. However, together CX516 (10 mg/kg) and Clozapine (1 mg/kg) produced a synergistic interaction, reducing methamphetamine-induced stereotypic rearing to a level nearly equivalent to that of vehicle-treated rats (no methamphetamine).

FIG. 2 provides a bar graph that shows total cumulative rearing activity during the 90 minute period after drug administration. Mean±standard error and number of animals for the experimental groups are as follows: saline, 56±9 n=12; METH (2 mg/kg), 724±136 n=20; METH+clozapine (1.0 mg/kg), 760±146 n=18; METH+CX516 (10 mg/kg), 495±78 n=19; METH+CX516+clozapine, 125±22 n=17 (** $p<0.0005$ vs METH+clozapine (1.0 mg/kg) by 2-tailed, unpaired t test assuming unequal variance; t test uses mean±standard deviation).

FIG. 3 shows the antagonistic effect of CX516 (30 mg/kg), haloperidol (HAL;0.06 mg/kg) or CX516 (30 mg/kg) combined with HAL (0.06 mg/kg) on rearing activity induced by methamphetamine. Neither CX516 (30 mg/kg) nor HAL (0.06 mg/kg) significantly reduced methamphetamine-induced rearing activity (23% and 16%, respectively). However, the combination of those same doses was synergistic, reducing methamphetamine-induced rearing activity by 67%.

FIG. 4 provides a bar graph that shows total rearing activity during the 90 minute test period. Mean rearing activity±standard error for the groups is as follows: saline: 53±11 n=16; METH: 1105±161, n=16; METH+HAL (0.06 mg/kg): 934±119, n=16; METH+CX516 (30 mg/kg): 863±169, n=16; METH+HAL+CX516: 360±77, n=16 (**p<0.0005 versus METH+HAL 0.06 mg/kg by 2-tailed, unpaired t test assuming unequal variance).

DETAILED DESCRIPTION OF THE INVENTION

Figure 1:
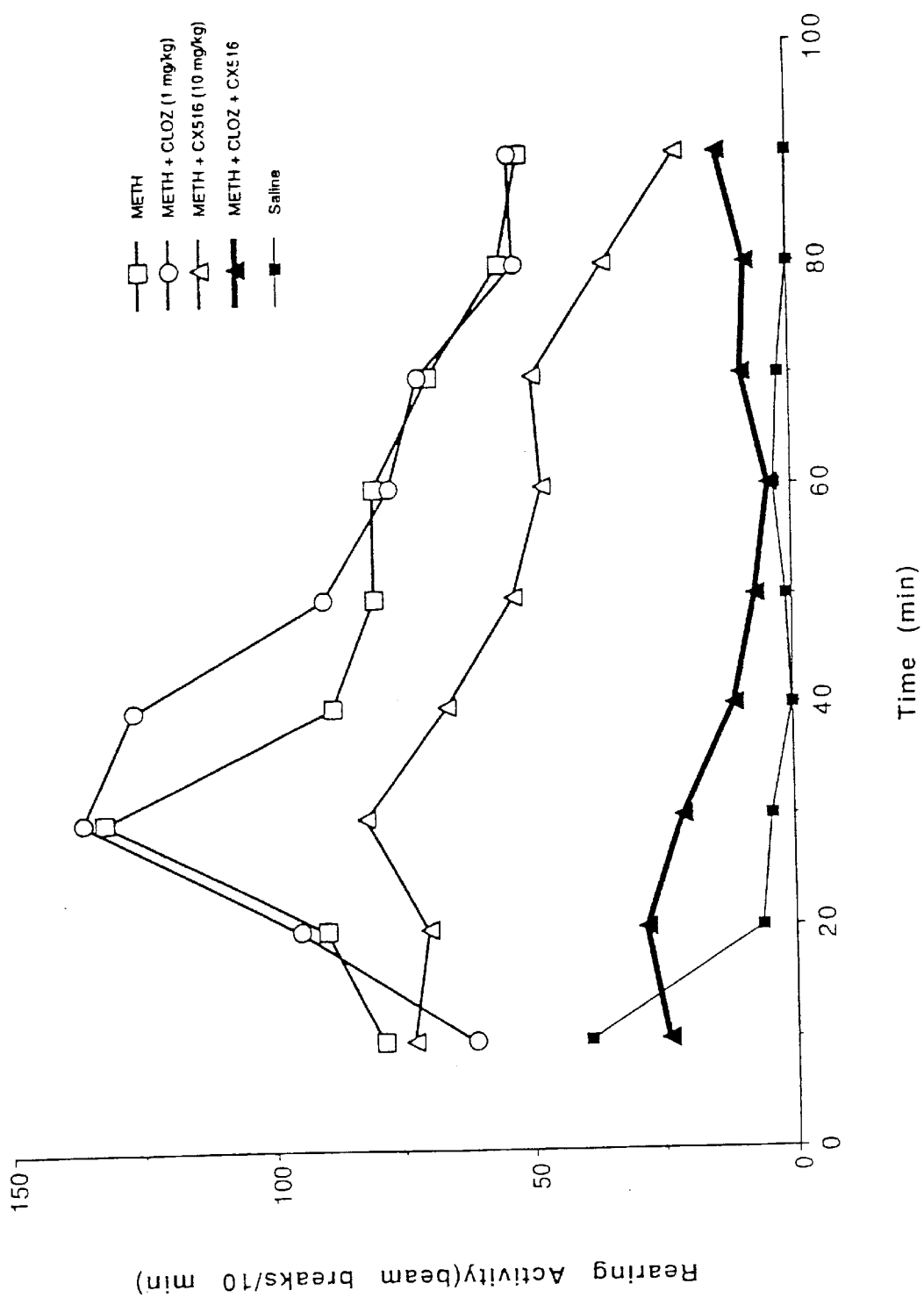
FIGS. 1 and 2 show that a representative Ampakine (CX516) synergistically enhances clozapine antagonism of methamphetamine-induced rearing activity.

The present invention is based on the discovery that synaptic responses mediated by AMPA receptors are increased by administration of a novel class of compounds known as Ampakines, disclosed in International Patent Application Publication No. WO 94/02475 (PCT/US93/069 16) (Lynch and Rogers, Regents of the University of California) and in related U.S. Pat. No. 5,773,434. The invention is particularly based on the discovery that compounds of the Ampakine family can interact with antipsychotics/neuroleptics in reversing behavior in animals in ways that predict success in treating subjects diagnosed as schizophrenics.

Ampakines primarily act, not by directly stimulating neural activation, but by upmodulating ("allosteric modulation") neural activation and transmission in neurons that contain glutamatergic receptors. These compounds bind to the glutamate receptor at a site other than the glutamate binding site, but such binding does not by itself give rise to ion fluxes. However, when a glutamate molecule binds to a glutamate receptor that has bound to it a glutamatergic compound of the invention, the subsequent ion flux is of much longer duration. Thus, in the presence of the compounds used herein, postsynaptic neurons are activated by much lower concentrations of glutamate than postsynaptic neurons that do not contain bound compounds.

Applications contemplated for Ampakines include improving the performance of subjects with sensory-motor problems dependent upon brain networks utilizing AMPA receptors; improving the performance of subjects impaired in cognitive tasks dependent upon brain networks utilizing AMPA receptors; improving the performance of subjects with memory deficiencies; and the like. Additional applications contemplated for Ampakines include restoring biochemical and synaptic balance between brain networks where an imbalance occurs due to decreased AMPA receptor currents. Such therapeutic uses would include, but are not limited to, psychiatric and neurological disorders such as schizophrenia and clinical depression.

In addition to data from animal and human studies that show that Ampakines improve cognitive performance, other tests, to be described below, indicate that Ampakines may eliminate the cortical/striatal imbalance known to occur in schizophrenia and to do so in a synergistic manner when administered with either typical or atypical antipsychotics/neuroleptics. The interaction with the antipsychotics in these animal models of schizophrenia is not only additive, but, surprisingly synergistic. These and other aspects and advantages of the invention will become apparent from the description that follows.

A. Definitions

Unless defined otherwise, all technical and scientific terms used herein have the same meaning as commonly understood by one of ordinary skill in the art to which this invention belongs. All references are incorporated by reference for all purposes. Although any methods and materials similar or equivalent to those described herein can be used in the practice or testing of the present invention, the preferred methods and materials are described. For purposes of the present invention, the following terms are defined below.

The term schizophrenia in the claims encompasses Schizophrenia or Schizophreniform Disorder or Schizoaffective Disorder or Delusional Disorder or Brief Psychotic Disorder or Psychotic Disorder Due to a General Medical Condition or Psychotic Disorder Not Otherwise Specified, and the symptoms of these disorders, are in large part as defined in the Diagnostic and Statistical Manual of Mental Disorder, fourth edition (DSMIV). The sections of the DSMIV that relate to these disorders are hereby incorporated by reference.

"Cyano" refers to the group —CN.

"Halogen" or "halo" refers to fluorine, bromine, chlorine, and iodine atoms.

"Hydroxy" refers to the group —OH.

"Thiol" or "mercapto" refers to the group —SH.

"Sulfamoyl" refers to the —$SO_2NH_2$.

"Alkyl" refers to a cyclic, branched or straight chain, alkyl group of one to eight carbon atoms. The term "alkyl" includes reference to both substituted and unsubstituted alkyl groups. This term is further exemplified by such groups as methyl, ethyl, n-propyl, i-propyl, n-butyl, t-butyl, i-butyl (or 2-methylpropyl), cyclopropylmethyl, cyclohexyl, i-amyl, n-amyl, and hexyl. Substituted alkyl refers to alkyl as just described including one or more functional groups such as aryl, acyl, halogen, hydroxyl, amido, amino, acylamino, acyloxy, alkoxy, cyano, nitro, thioalkyl, mercapto and the like. These groups may be attached to any carbon atom of the lower alkyl moiety. "Lower alkyl" refers to $C_1$–$C_6$ alkyl, with $C_1$–$C_4$ alkyl more preferred. "Cyclic alkyl" includes both mono-cyclic alkyls, such as cyclohexyl, and bi-cyclic alkyls, such as [3.3.0]bicyclooctane and [2.2.1] bicycloheptane. "Fluoroalkyl" refers to alkyl as just described, wherein some or all of the hydrogens have been replaced with fluorine (e.g., —$CF_3$ or —$CF_2CF_3$).

"Aryl" or "Ar" refers to an aromatic substituent which may be a single ring or multiple rings which are fused together, linked covalently, or linked to a common group such as an ethylene or methylene moiety. The aromatic ring(s) may contain a heteroatom, such as phenyl, naphthyl, biphenyl, diphenylmethyl, 2,2-diphenyl-1-ethyl, thienyl, pyridyl and quinoxalyl. The term "aryl" or "Ar" includes reference to both substituted and unsubstituted aryl groups. If substituted, the aryl group may be substituted with halogen atoms, or other groups such as hydroxy, cyano, nitro, carboxyl, alkoxy, phenoxy, fluoroalkyl and the like. Additionally, the aryl group may be attached to other moieties at any position on the aryl radical which would otherwise be occupied by a hydrogen atom (such as 2-pyridyl, 3-pyridyl and 4-pyridyl).

The term "alkoxy" denotes the group —OR, where R is lower alkyl, substituted lower alkyl, aryl, substituted aryl, aralkyl or substituted aralkyl as defined below.

The term "acyl" denotes groups —C(O)R, where R is alkyl, substituted alkyl, alkoxy, aryl, substituted aryl, amino and alkylthiol.

"Carbocyclic moiety" denotes a ring structure in which all ring vertices are carbon atoms. The term encompasses both single ring structures and fused ring structures. Examples of aromatic carbocyclic moieties are phenyl and naphthyl.

"Heterocyclic moiety" denotes a ring structure in which one or more ring vertices are atoms other than carbon atoms, the remainder being carbon atoms. Examples of non-carbon atoms are N, O, and S. The term encompasses both single ring structures and fused ring structures. Examples of aromatic heterocyclic moieties are pyridyl, pyrazinyl, pyrimidinyl, quinazolyl, isoquinazolyl, benzofuryl, isobenzofuryl, benzothiofuryl, indolyl, and indolizinyl.

The term "amino" denotes the group NRR', where R and R' may independently be hydrogen, lower alkyl, substituted lower alkyl, aryl, substituted aryl as defined below or acyl.

The term "amido" denotes the group —C(O)NRR', where R and R' may independently be hydrogen, lower alkyl, substituted lower alkyl, aryl, substituted aryl as defined below or acyl.

The term "independently selected" is used herein to indicate that the two R groups, $R^1$ and $R^2$, may be identical or different (e.g., both $R^1$ and $R^2$ may be halogen or, $R^1$ may be halogen and $R^2$ may be hydrogen, etc.).

The term "subject" means a mammal, particularly a human. The term specifically includes domestic and common laboratory mammals, such as non-human primates, kine, horses, pigs, goats, sheep, rabbits, rats and mice.

"α-amino-3-hydroxy-5-methyl-isoxazole-4-propionic acid", or "AMPA", or "glutamatergic" receptors are molecules or complexes of molecules present in cells, particularly neurons, usually at their surface membrane, that recognize and bind to glutamate or AMPA. The binding of AMPA or glutamate to an AMPA receptor normally gives rise to a series of molecular events or reactions that result in a biological response. The biological response may be the activation or potentiation of a nervous impulse, changes in cellular secretion or metabolism, or causing cells to undergo differentiation or movement.

The term "central nervous system" or "CNS" comprises the brain and the spinal cord. The term "peripheral nervous system" or "PNS" comprises all parts of the nervous system that are not part of the CNS, including cranial and spinal nerves and the autonomic nervous system.

The phrase "effective amount" means a dosage sufficient to produce a desired result. Generally, the desired result is a subjective or objective decrease in the symptoms of schizophrenia, as measured by the techniques described below.

B. Compounds Used to Treat Schizophrenia

Compounds useful in the practice of this invention are generally those which amplify (upmodulate) the activity of the natural stimulators of AMPA receptors, particularly by amplifying excitatory synaptic response. We describe herein a wide variety of diverse compounds suitable for use in the invention. Methods for identifying other compounds are routine. They involve a variety of accepted tests to determine whether a given candidate compound is an upmodulator of the AMPA receptor. The primary assay is measurement of enlargement of the excitatory postsynaptic potential (EPSP) in in vitro brain slices, such as rat hippocampal brain slices.

In experiments of this kind, slices of hippocampus from a mammal such as rat are prepared and maintained in an interface chamber using conventional methods. Field EPSPs are recorded in the stratum radiatum of region CA1b and elicited by single stimulation pulses delivered once per 20 seconds to a bipolar electrode positioned in the Schaffer-commissural projections (see Granger et al., 1993, *Synapse*, 15:326–329; Staubli et al., 1994a, *Proc. Nat. Acad. Sci.*, 91:777–781; and Staubli, V. et al., 1994b, *Proc. Nat. Acad. Sci.*, 91:11158–11162; Arai et al., 1994, *Brain Res.*, 638:343–346; Arai et al., "Effects of a centrally active drug on AMPA receptor kinetics).

The wave form of a normal EPSP is composed of:

an AMPA component, which has a relatively rapid rise time in the depolarizing direction (~5–10 msec) and which decays within ~20 msec.;

an NMDA component (slow ~30–40 msec rise time and slow ~40–70 msec decay) (the NMDA portion will not appear in normal CSF media, due to the voltage requirement for NMDA receptor channel activation, but in low magnesium media, an NMDA component may appear;

a GABA component in the opposite (hyperpolarizing) direction as the glutamatergic (AMPA and NMDA) components, exhibiting a time course with a rise time of ~10–20 msec and very slow decay (~50–100 msec or more).

The different components can be separately measured to assay the effect of a putative AMPA receptor enhancing agent. This is accomplished by adding agents that block the unwanted components, so that the detectable responses are essentially only AMPA responses. For example, to measure AMPA responses, an NMDA receptor blocker (e.g., AP-5 or other NMDA blockers known in the art) and/or a GABA blocker (e.g., picrotoxin or other GABA blockers known in the art) are added to the slice. To prevent epileptiform activity in the GABA-blocked slices, known agents such as tetrodotoxin may be used.

AMPA upmodulators useful in the present invention are substances that cause an increased ion flux through the AMPA receptor complex channels in response to glutamatergic stimulation. Increased ion flux is typically measured as one or more of the following non-limiting parameters: at least a 10% increase in decay time, amplitude of the waveform and/or the area under the curve of the waveform and/or a decrease of at least 10% in rise time of the waveform, for example in preparations treated to block NMDA and GABA components. The increase or decrease is preferably at least 25–50%; most preferably it is at least 100%. How the increased ion flux is accomplished (e.g., increased amplitude or increased decay time) is of secondary importance; upmodulation is reflective of increased ion fluxes through the AMPA channels, however achieved.

An additional and more detailed assay is that of excised patches, i.e., membrane patches excised from cultured hippocampal slices; methods are described in Arai et al., 1994. Outside-out patches are obtained from pyramidal hippocampal neurons and transferred to a recording chamber. Glutamate pulses are applied and data are collected with a patch clamp amplifier and digitized (Arai et al., 1994).

Because these membrane patches should contain only glutamatergic receptors, GABAergic currents will not be seen. Any NMDA currents can be blocked as above (e.g., with AP-5).

The central action of a drug can be verified by measurement of Field EPSPs in behaving animals (see Staubli et al., 1994a) and time course of biodistribution can be ascertained via injection and PET measurement of radiolabeled drug (see Staubli et al., 1994b).

One such class of compounds is defined by Formula I:

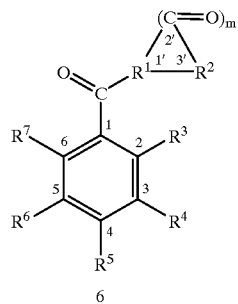

(I)

In this formula:

$R^1$ is either N or CH;

m is either 0 or 1;

$R^2$ is either $(CR^8{}_2)_{n-m}$ or $C_{n-m}R^8{}_{2(n-m)-2}$, in which:
  n is 4, 5, 6, or 7; and
  the $R^8$'s in any single compound are either the same or different, each $R^8$ being either H or $C_1$–$C_6$ alkyl, or one $R^8$ being combined with either $R^3$ or $R^7$ to form a single bond bridging the no. 3' and either the no. 2 or the no. 6 ring vertices or a single divalent linking moiety linking the no. 3' and either the no. 2 or the no. 6 ring vertices, examples of single divalent linking moieties being $CH_2$, $CH_2$, $CH_2$—$CH_2$, CH=CH, O, NH, $N(C_1$–$C_6$ alkyl), N=CH, N=C($C_1$–$C_6$ alkyl), C(O), O—C(O), C(O)—O, CH(OH), NH—C(O), and $N(C_1$–$C_6$ alkyl)—C(O);

$R^3$, when not combined with any $R^8$, is either H, $C_1$–$C_6$ alkyl, or $C_1$–$C_6$ alkoxy;

$R^4$ is either H, OH, or $C_1$–$C_6$ alkoxy, or is combined with $R^5$;

$R^5$ is either combined with $R^4$ or is H, OH, $C_1$–$C_6$ alkoxy, amino, mono($C_1$–$C_6$ alkyl)amino, di($C_1$–$C_6$ alkyl)amino, or $CH_2OR^9$, in which:
  $R^9$ is H, $C_1$–$C_6$ alkyl, an aromatic carbocyclic moiety, an aromatic heterocyclic moiety, an aromatic carbocyclic alkyl moiety, an aromatic heterocyclic alkyl moiety, or any such moiety substituted with one or more members of the group $C_1$–$C_3$ alkyl, $C_1$–$C_3$ alkoxy, hydroxy, halo, amino, alkylamino, dialkylamino, and methylenedioxy;

$R^6$ is either H or $CH_2OR^9$;

$R^4$ and $R^5$ when combined form a member selected from the group consisting of

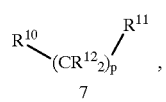

7

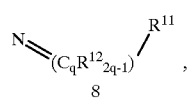

8

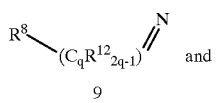

9

-continued

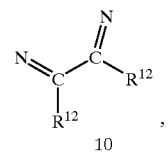

10 in which:
$R^{10}$ is either O, NH or $N(C_1$–$C_6$ alkyl);
$R^{11}$ is either O, NH or $N(C_1$–$C_6$ alkyl);
$R^{12}$ is either H or $C_1$–$C_6$ alkyl, and when two or more $R^{12}$'s are present in a single compound, such $R^{12}$'s are the same or different;
p is 1, 2, or 3; and
q is 1 or 2; and
$R^7$, when not combined with any $R^8$, is either H, $C_1$–$C_6$ alkyl, or $C_1$–$C_6$ alkoxy.

Within the scope of Formula I, certain subclasses are preferred. One of these is the subclass in which $R^2$ is $(CHR^8)_{n-m}$ or $C_{n-m}HR^8{}_{2(n-m)-3}$, and $R^3$ is H, $C_1$–$C_6$ alkyl, or $C_1$–$C_6$ alkoxy. Another is the subclass in which $R^2$ is $(CHR^8)_{n-m}$ or $C_{n-m}HR^8{}_{2(n-m)-3}$, and one $R^8$ is combined with either $R^3$ or $R^7$ to form a single bond bridging the 2 and 3' ring vertices or a single divalent linking moiety linking the 2 and 3' ring vertices, with $CH_2$, $CH_2$—$CH_2$, CH=CH, O, NH, $N(C_1$–$C_6$ alkyl), N=CH, N=C($C_1$–$C_6$ alkyl), C(O), O—C(O), C(O)—O, CH(OH), NH—C(O), and $N(C_1$–$C_6$ alkyl)—C(O) as the linking moiety. A preferred subclass of $R^2$ is $CHR^8$—$CH_2$—$CH_2$—$CH_2$ and $CHR^8$—$CH_2$—$CH_2$—$CH_2$—$CH_2$. A preferred subclass of linking moieties is $CH_2$, $CH_2$—$CH_2$, CH=CH, O, NH, C(O), and CH(OH). A further preferred subclass is $CH_2$, O, NH, C(O), and CH(OH).

When $R^4$ and $R^5$ are combined, a preferred subclass for $R^{12}$ is H and $CH_3$, and preferred groups representing the combination of $R^4$ and $R^5$ are

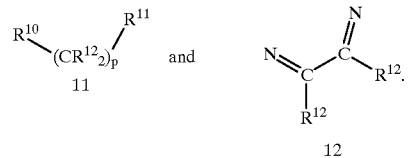

11

12

In these groups, $R^{10}$ and $R^{11}$ are both preferably O, and p is 1 or 2. Still further preferred subclasses are those in which m is zero.

A further class of compounds useful in the practice of the invention are those of Formula II:

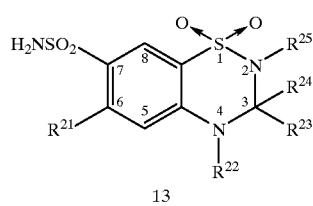

II

13

In Formula II:
$R^{21}$ is either H, halo or $CF_3$;
$R^{22}$ and $R^{23}$ either are both H or are combined to form a double bond bridging the 3 and 4 ring vertices;
$R^{24}$ is either H, $C_1$–$C_6$ alkyl, $C_5$–$C_7$ cycloalkyl, $C_5$–$C_7$ cycloalkenyl, Ph, $CH_2Ph$, $CH_2SCH_2Ph$, $CH_2X$, $CHX_2$, CH₂SCH₂CF₃, CH₂SCH₂CH═CH₂, or

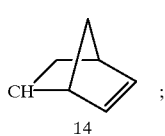

and R²⁵ is a member selected from the group consisting of H and C₁–C₆ alkyl.

Within the scope of Formula II, certain subclasses are preferred. One of these is the subclass in which R²¹ is Cl or CF₃, with Cl preferred. Another is the subclass in which all X's are Cl. Still another is the subclass in which R²² and R²³ are both H. A preferred subclass of R²⁴ is that which includes CH₂Ph, CH₂SCH₂Ph, and

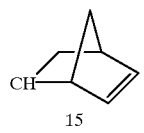

Preferred compounds within the scope of Formula II are those in which R²⁴ is either C₅–C₇ cycloalkyl, C₅–C₇ cycloalkenyl or Ph ("Ph" denotes a phenyl group). Other preferred compounds of this group are those in which R²¹ is halo, R²² is H, R²³ is H, and R²⁵ is H. Preferred substituents for R²⁴ are cyclohexyl, cyclohexenyl, and phenyl.

Compounds 1 through 25 below are examples of compounds within the scope of Formula I:

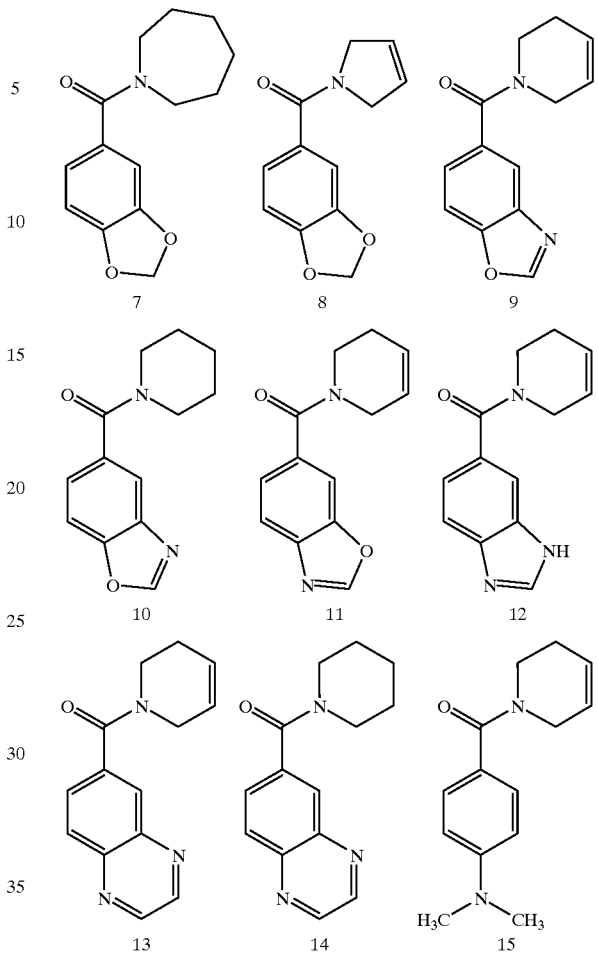

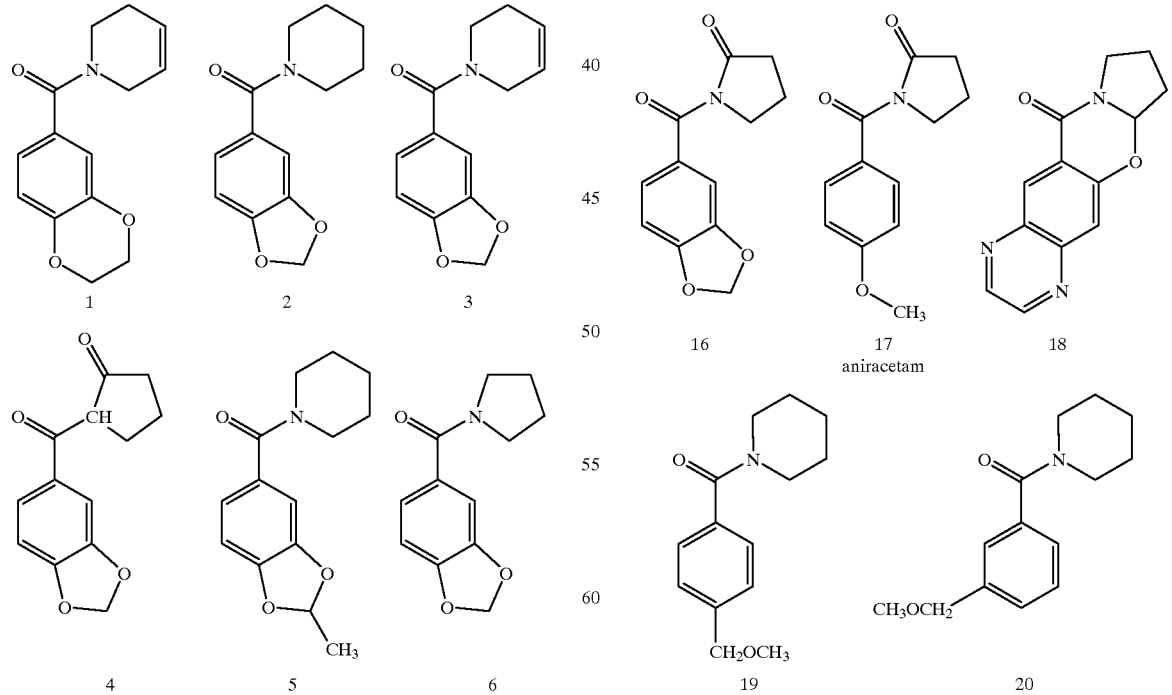

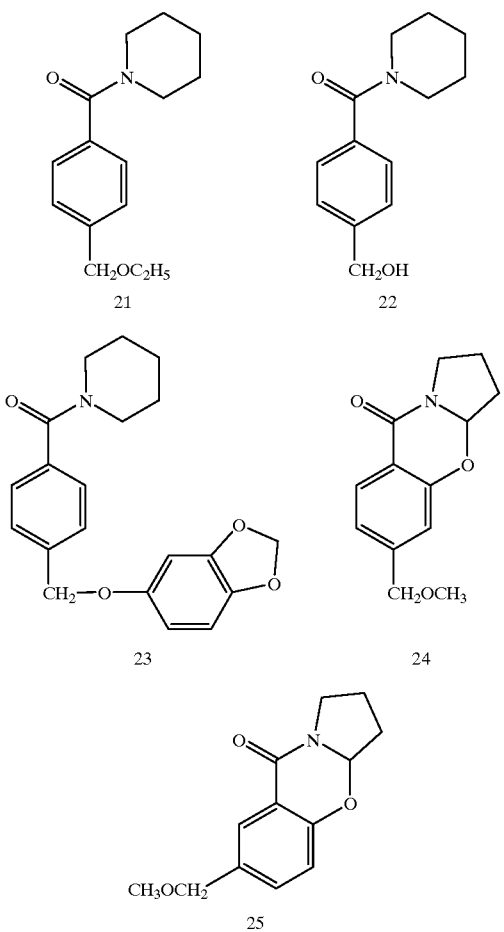
Compounds 26 through 40 below are compunds within the scope of Formula II:
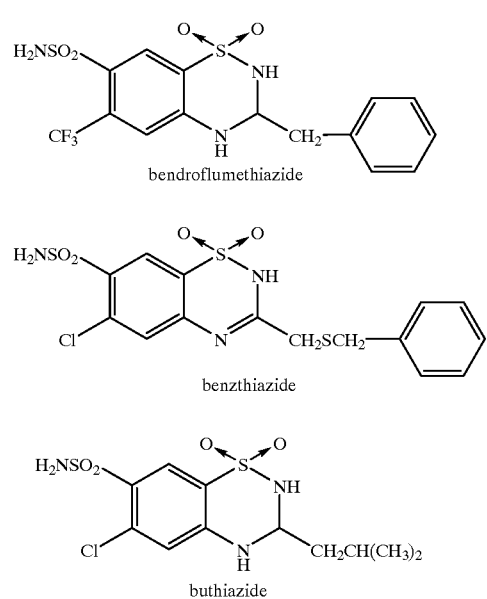
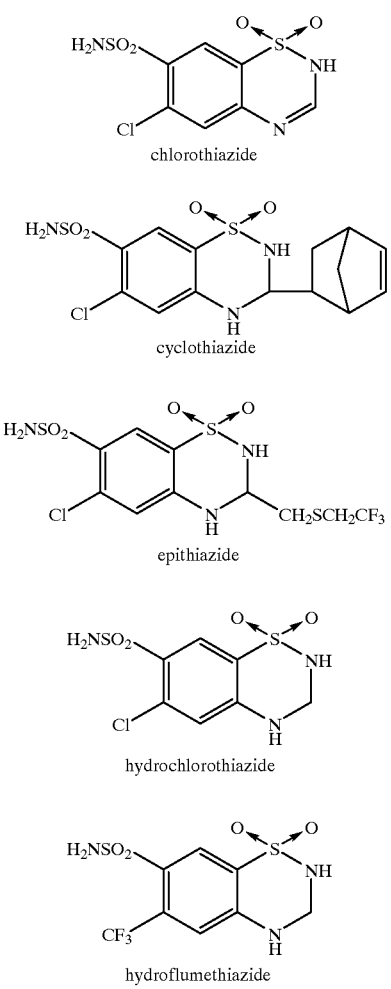

-continued

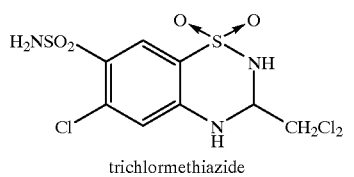
trichlormethiazide 37

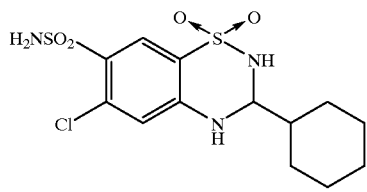 38

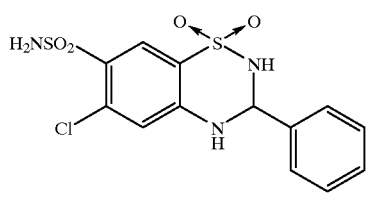 39

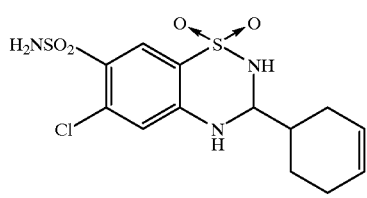 40

A particularly preferred compound is compound CX516, 1-(Quinoxalin-6-ylcarbonyl)piperidine, having the following structure:

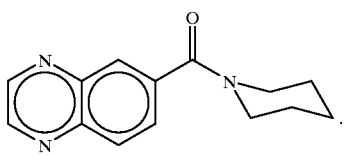

In another embodiment, the Ampakine is a compound of formula III:

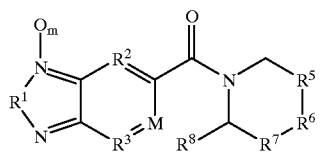
III in which:

R$^1$ is oxygen or sulfur;
R$^2$ and R$^3$ are independently selected from the group consisting of —N=, —CR=, and —CX=;
M is =N or =CR$^4$—, wherein R$^4$ and R$^8$ are independently R or together form a single linking moiety linking M to the ring vertex 2', the linking moiety being selected from the group consisting of a single bond, —CR$_2$—, —CR=CR—, —C(O)—, —O—, —S(O)$_y$—, —NR—, and —N=;

R$^5$ and R$^7$ are independently selected from the group consisting of —(C$_2$)$_n$—, —C(O)—, —CR=CR—, —CR=CX—, —C(RX)—, —CX$_2$—, —S—, and —O—; and
R$^6$ is selected from the group consisting of —(CR$_2$)$_m$—, —C(O)—, —CR=CR—, —C(RX)—, —CR$_2$—, —S—, and —O—;
wherein
X is —Br, —Cl, —F, —CN, —NO$_2$, —OR, —SR, —NR$_2$, —C(O)R—, —CO$_2$R, or —CONR$_2$; and
R is hydrogen, C$_1$–C$_6$ branched or unbranched alkyl, which may be unsubstituted or substituted with one or more functionalities defined above as X, or aryl, which may be unsubstituted or substituted with one or more functionalities defined above as X;
m and p are independently 0 or 1;
n and y are independently 0, 1 or 2.

Preferred embodiments include:

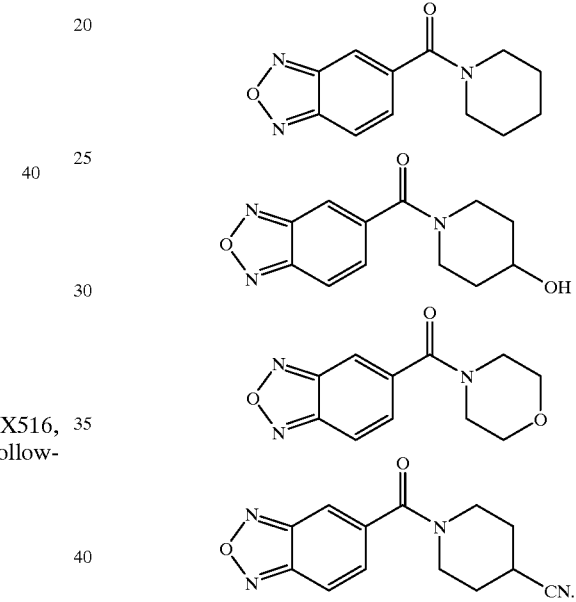

1. Preparation of Formula I Compounds

The compounds described above are prepared by conventional methods known to those skilled in the art of synthetic organic chemistry. For example, certain compounds of Formula I are prepared from an appropriately substituted benzoic acid by contacting the acid under conditions suitable to activate the carboxy group for the formation of an amide. This is accomplished, for example, by activating the acid with carbonyl diimidazole, or with a chlorinating agent such as thionyl chloride or oxalyl chloride to obtain the corresponding benzoyl chloride. The activated acid is then contacted with a nitrogen-containing heterocyclic compound under conditions suitable for producing the desired imide or amide. Alternatively, the substituted benzoic acid is ionized by contact with at least two equivalents of base such as triethylamine in an inert solvent such as methylene chloride or alcohol-free chloroform, and the ionized benzoic acid can then be reacted with pivaloyl chloride or a reactive carboxylic acid anhydride such as trifluoroacetic anhydride or trichloroacetic anhydride, to produce a mixed anhydride. The mixed anhydride is then contacted with a nitrogen-containing heterocyclic compound to produce the desired imide or amide.

A further alternative to these methods, suitable for some of the compounds of Formula I, is to contact the appropriately selected 3,4-(alkylenedihetero)-benzaldehyde with ammonia to form an imine, then contacting the imine with benzoyloxycarbonyl chloride to form the benzoyloxycarbonyl imine. Suitable 3,4-(alkylenedihetero)-benzaldehydes include 3,4-(methylenedioxy)-benzaldehyde, 3,4-(ethylenedioxy)-benzaldehyde, 3,4-(propylenedioxy)-benzaldehyde, 3,4-(ethylidenedioxy)-benzaldehyde, 3,4-(propylenedithio)-benzaldehyde, 3,4-(ethylidenedithio)-benzaldehyde, 5-benzimidazolecarboxaldehyde, and 6-quinoxalinecarboxaldehyde. The benzoyloxycarbonyl imine is then contacted with a simple conjugated diene such as butadiene under cycloaddition reaction conditions, and then with a Lewis acid under conditions suitable for a Friedel-Crafts acylation. Examples of suitable conjugated dienes include butadiene, 1,3-pentadiene, and isoprene, and examples of suitable Lewis acids include $AlCl_3$ and $ZnCl_2$.

Still further compounds within Formula I are prepared from 2,3-dihydroxy naphthalene. This starting material is reacted with 1,2-dibromoethane in the presence of base to produce an ethylenedioxy derivative of naphthalene, which is then reacted with an oxidizing agent such as potassium permanganate to produce 4,5-ethylenedioxyphthaldehydic acid. The latter is contacted with anhydrous ammonia to form an imine, which is then treated with a suitable carbonyl-activating agent such as dicyclohexylcarbodiimide under cyclization conditions to form an acyl imine. The acyl imine is then reacted with a simple conjugated diene to achieve cycloaddition.

Still further compounds within Formula I are prepared by contacting an α-halotoluic acid with at least two equivalents of an alkali salt of a lower alcohol according to the Williamson ether synthesis to produce an ether linkage. The resulting alkoxymethylbenzoic acid is activated with carbonyldiimidazole, thionyl chloride, dicyclohexylcarbodiimide, or any other suitable activating agent, and reacted with a suitable amine to achieve a carboxamide linkage.

In an alternate to the scheme of the preceding paragraph, a formyl-substituted aromatic carboxamide is prepared by activation of an appropriate starting acid with a tertiary amine (for example, triethyl amine) plus an acid chloride (for example, pivaloyl chloride) to produce a mixed anhydride for coupling to a suitable amine. The formyl group is then reduced to an alcohol by a suitable reducing agent such as sodium borohydride. The alcohol is then converted to a leaving group which is replaceable by the alkali salt of an alcohol. The leaving group can be generated by reagents such as thionyl chloride, thionyl bromide, mineral acids such as hydrochloric, hydrobromic or hydroiodic acids, or the combined action of a tertiary amine plus either a suitable sulfonic anhydride or sulfonyl halide. Alternatively, the alcohol is activated by removing the proton. This is achieved by the action of a strong base such as sodium hydride in an aprotic solvent such as dimethylformamide. The resulting alkoxide is then reacted with a suitable alkyl halide or other alkyl compound with a suitable leaving group to produce the desired ether linkage.

Fused ring structures such as those in which $R^3$ and one of the $R^8$'s of Formula I are combined to form a single linking group bridging the 2 and 3' carbon atoms can be synthesized in the following manner. The carboxyl group of an appropriately substituted salicylic acid is activated with carbonyldiimidazole in dichloromethane, chloroform, tetrahydrofuran, or other anhydrous solvent. An aminoalkylacetal such as $H_2N(CH_2)_3CH(OCH_2CH_3)_2$ is added. The resulting amide is treated with an aryl or alkyl sulfonic acid, trifluoroacetic acid, or other strong acid, in a solvent of low basicity such as chloroform or dichloromethane, to cleave the acetal and cyclize the intermediate aldehyde with the amide nitrogen and the phenolic oxygen.

In all of these reaction schemes, the methods and reaction conditions for each of the individual reactions are well within the routine skill of, and will be readily apparent to, the synthesis chemist.

2. Preparation of Formula II Compounds

Compounds of Formula II and methods for their preparation are described in the literature. These methods are within the routine skill of the synthesis chemist. The preparation of compounds such as bendroflumethiazide, for example, is described by Goldberg (Squibb), in U.S. Pat. No. 3,265,573 (1966). The preparation of compounds such as benzthiazide, epithiazide, methalthiazide and polythiazide is described by McManus (Pfizer), U.S. Pat. No. 3,009,911 (1961). The preparation of buthiazide is described in U.K. Patent Nos. 861,367 and 885,078 (Ciba, 1961). The preparation of chlorothiazide is described by Hinkley (Merck & Co.), U.S. Pat. Nos. 2,809,194 (1957) and 2,937,169 (1960). The preparation of hydrochlorothiazide is described by Novello (Merck & Co.), U.S. Pat. No. 3,025,292 (1962); de Stevens and Werner (Ciba), U.S. Pat. No. 3,163,645 (1964); and Irons et al. (Merck & Co.), U.S. Pat. No. 3,164,588 (1965). The preparation of hydroflumethiazide is described by Lund et al. (Lovens), U.S. Pat. No. 3,254,076 (1966). The preparation of methylclothiazide is described by Close et al., 1960, *J. Am. Chem. Soc.,* 82:1132. The preparation of trichlormethiazide is described by de Stevens et al, 1960, *Experientia,* 16:113. The disclosures of each of these patents and papers is incorporated herein by reference.

3. Screening of Compounds

A number of compounds belonging to the above-described genus have been shown to up-modulate glutamatergic transmission by augmenting ligand-AMPA receptor complex-activated ion gating. Staubli, U. et al., 1994a, *Proc. Nat. Acad. Sci. U.S.A.,* 91:777–781; Staubli, U. et al., 1994b, *Proc. Nat. Acad. Sci. U.S.A.,* 91:11158–11162; Arai, A. et al., 1994, *Brain Res.,* 638:343–346; Granger, R. et al., 1993, *Synapse,* 15:326–329; all of which are incorporated by reference. These compounds rapidly cross the blood-brain barrier (Staubli, U. et al., 1994b) and increase ESPSs in freely moving rats (Staubli, U. et al., 1994a). Animal experiments indicate that these centrally active modulators improve memory in both rat (Granger, R. et al., 1993; Staubli, U. et al., 1994a) and human models (Lynch et al., 1996, *Internat. Clinical Psychopharmacology* 11:13; Ingvar et al., 1997, *Exp. Neurol.* 146: 553–559, both of which are incorporated by reference).

Once prepared, the compounds of this invention are screened for their ability to amplify (upmodulate) the activity of the natural stimulators of AMPA receptors, particularly by amplifying excitatory synaptic responses. A variety of accepted tests are used to determine whether a given compound is an upmodulator of the AMPA receptor. The primary assay is measurement of the enlargement of the excitatory postsynaptic potential (EPSP) in in vitro brain slices, such as rat hippocampal brain slices.

In experiments of this kind, slices of hippocampus from a mammal, such as rat, are prepared and maintained in an interface chamber using conventional methods. Field EPSPs are recorded in the stratum radiatum of region CA1b and elicited by single stimulation pulses delivered once per 20 seconds to a bipolar electrode positioned in the Schaffer-commissural projections (see, Granger, R. et al., *Synapse,* 15:326–329 1993; Staubli, U. et al., 1994a, *Proc. Nat. Acad. Sci.,* 91:777–781; and Staubli, V. et al., 1994b, *Proc. Nat.*

Acad. Sci., 91:11158–11162; Arai, A. et al., 1994, *Brain Res.*, 638:343–346; Arai, A. et al., "Effects of a centrally active drug on AMPA receptor kinetics, submitted). The wave form of a normal EPSP is composed of an AMPA component, which has a relatively rapid rise time in the depolarizing direction (~5–10 msec) and which decays within ~20 msec.; an NMDA component (slow ~30–40 msec rise time and slow ~40–70 msec decay) (the NMDA portion will not appear in normal or artificial CSF (cerebro-spinal fluid) media, due to the voltage requirement for NMDA receptor channel activation, but in low magnesium media, an NMDA component may appear; a GABA (gamma-aminobutyric acid) component in the opposite (hyperpolarizing) direction as the glutamatergic (AMPA and NMDA) components, exhibiting a time course with a rise time of ~10–20 msec and very slow decay (~50–100 msec or more).

The different components are separately measured to assay the effect of a putative AMPA receptor enhancing agent. This is accomplished by adding agents that block the unwanted components, so that the detectable responses are essentially only AMPA responses. For example, to measure AMPA responses, an NMDA receptor blocker (e.g., AP-5 or other NMDA blockers known in the art) and/or a GABA blocker (e.g., picrotoxin or other GABA blockers known in the art) are added to the slice. To prevent epileptiform activity in the GABA-blocked slices, known agents such as tetrodotoxin may be used.

AMPA upmodulators useful in the present invention are substances that cause an increased ion flux through the AMPA receptor complex channels in response to glutamatergic stimulation. Increased ion flux is typically measured as one or more of the following non-limiting parameters: at least a 10% increase in decay time, amplitude of the waveform and/or the area under the curve of the waveform and/or a decrease of at least 10% in rise time of the waveform, for example in preparations treated to block NMDA and GABA components. The increase or decrease is preferably at least 25–50%; most preferably it is at least 100%. How the increased ion flux is accomplished (e.g., increased amplitude or increased decay time) is of secondary importance; upmodulation is reflective of increased ion fluxes through the AMPA channels, however achieved.

An additional and more detailed assay is that of excised patches, i.e., membrane patches excised from cultured hippocampal slices; methods are described in Arai et al, 1994. Outside-out patches are obtained from pyramidal hippocampal neurons and transferred to a recording chamber. Glutamate pulses are applied and data are collected with a patch clamp amplifier and digitized (Arai et al., 1994). Because no GABA is applied to the patch, GABAergic currents will not be elicited. Any NMDA currents are blocked as above (e.g., with AP-5).

The central action of a drug is verified by measurement of field EPSPs in behaving animals (see, Staubli et al., 1994a) and time course of biodistribution can be ascertained via injection and subsequent quantitation of drug levels in various tissue samples. Quantitation is accomplished by methods known to those skilled in the art and will vary depending on the chemical nature of the drug.

C. Other Compounds

The above described genus and species of compounds represent merely one example of glutamatergic compounds that may be used to treat schizophrenia according to the present invention. The treatments provided by present invention are not limited to the compounds described above. The present invention also encompasses administering other compounds that enhance the stimulation of α-amino-3-hydroxy-5-methyl-isoxazole-4-propionic acid ("AMPA") receptors in a subject, said enhancement being sufficient to diminish the symptoms of schizophrenia. Examples of other such AMPA-selective compounds include 7-chloro-3-methyl-3-4-dihydro-2H-1,2,4 benzothiadiazine S,S, dioxide, as described in Zivkovic et al., 1995, *J. Pharmacol. Exp. Therap.*, 272:300–309; Thompson et al., 1995, *Proc. Nat. Acad. Sci. USA*, 92:7667–7671.

The methods of the present invention also involve the administration of antipsychotic medications. Antipsychotic medications (this term is used interchangeably with the term neuroleptics) are a class of compounds that include haloperidol and atypical members such as clozapine, olanzapine and risperidone. Chiodo et al., (1983) "Typical and atypical neuroleptics: differential effects of chronic administration on the activity of A-9 and A-10 midbrain dopaminergic neurons," *J. Neurosci.* 3:1607–1609; Ljungberg et al. (1978), "Classification of neuroleptic drugs according to their ability to inhibit apomorphine-induced locomotion and gnawing: evidence for two different mecahnisms of action," *Psychopharmacology* 56:239–247; Lynch et al., (1988), Sensitization of chronic neuroleptic behavioral effects, *Biol. Psychiatry*, 24:950–951; Rupniak et al. (1985), "Mesolimbic dopamine function is not altered during continuous chronic treatment of rats with typical or atypical neuroleptic drugs," *J. Neural. Transm.* 62:249–266; Sayers et al. (1975), "Neuroleptic-induced hypersensitivity of striatal dopamine receptors in the rat as a model of tardive dyskinesia. Effects of clozapine, haloperidol, loxapine and chloropromazine," *Psychopharmacologia* 41:97–104; Titeler et al., (1980), "Radioreceptor labeling of pre- and post-synaptic receptors." In Cattabeni et al. (eds), "Long-term effects of neuroleptics." Raven Press, New York, *Adv. Biochem. Psychopharmacol.* 24:159166; Wyatt, R. J. (1976), Biochemistry and schizophrenia (part IV): the neuroleptics—their mechanism of action: A review of the biochemical literature. *Psychopharmacol. Bull.* 12:5–50.

D. Subject Selection

Subjects contemplated for treatment in accordance with this invention include humans, laboratory animals, and domestic animals. In particular, human subjects are individuals that exhibit symptoms of Schizophrenia or Schizophreniform Disorder or Schizoaffective Disorder or Delusional Disorder or Brief Psychotic Disorder or Psychotic Disorder Due to a General Medical Condition or Psychotic Disorder Not Otherwise Specified, as defined in the Diagnostic and Statistical Manual of Mental Disorder, third edition (DSMIV).

E. Administration of Compounds

The compounds of this invention are incorporated into a variety of formulations for therapeutic administration. Examples are capsules, tablets, syrups, suppositories, and various injectable forms. Administration of the compounds is achieved in various ways, including oral, bucal, rectal, parenteral, intraperitoneal, intradermal, transdermal, etc., administration. Preferred formulations of the compounds are oral preparations, particularly capsules or tablets.

F. Dosage

The above described compounds and/or compositions are administered at a dosage that diminishes the symptoms of schizophrenia and related disorders (see above) in subjects suffering from these disorders, while at the same time minimizing any side-effects. It is contemplated that the composition will be obtained and used under the guidance of a physician.

Typical dosages for systemic Ampakine administration range from about 0.1 to about 1000 milligrams per kg weight of subject per administration. A typical dosage may be one 10–500 mg tablet taken once a day, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Dose levels can vary as a function of the specific compound, the severity of the symptoms, and the susceptibility of the subject to side effects. Some of the specific compounds that stimulate glutamatergic receptors are more potent than others. Preferred dosages for a given compound are readily determinable by those of skill in the art by a variety of means. A preferred means is to measure the physiological potency of a given compound that is a candidate for administration, by the method of Davis et al. (1996), submitted to Behavioral Neuroscience. Briefly, excised patches and excitatory synaptic responses are measured in the presence of different concentrations of test compounds, and the differences in dosage response potency are recorded and compared. Davis et al. found that one specific compound designated BDP-20 was about ten-fold more potent than another designated BDP-12 in a variety of behavioral (exploratory activity, speed of performance) and physical (excised patches and excitatory synaptic responses) tests. The relative physiological potency was an accurate measure of their behavioral potency. Thus, excised patches and excitatory synaptic responses may be used to gauge the relative physiological (and behavioral) potency of a given compound with regard to a known standard.

Glutamatergic compounds for the treatment of schizophrenia may have a half-life measured from less than 10 minutes to more than 2 hours. In some embodiments, the compound preferably has a rapid onset and short elimination half-life ($\leq 90$ min.).

In the present invention, the Ampakines are typically administered together with antipsychotic compounds. Although the antipsychotic drugs are effective in their normal therapeutic range compounds are preferably administered close to or at subtherapeutic doses, i.e., doses lower than the doses typically used for administration of the antypsychotic by itself to treat disorders such as schizophrenia. See, e.g., U.S. Pat. No. 5,602,150. The range of therapeutically effective doses for mammalian subjects may range from about 0.1 to about 2000 mg per kilogram of body weight per day, or preferably between about 1 mg/kg to about 500 mg/kg of body weight per day, more preferably between about 10 mg/kg to about 250 mg/kg, depending on the particular neuroleptic administered, route of administration, dosage schedule and form, and general and specific responses to the drug. For convenience, the total daily dosage may be divided and administered in portions throughout the day, if desired. The therapeutically effective dose of antipsychotic drugs administered to adult human patients also depends on the route of administration, the age, weight and condition of the individual. Some patients who fail to respond to one drug may respond to another, and for this reason, several drugs may have to be tried to find the one most effective for an individual patient. Some therapeutic doses are shown below:

| ANTIPSYCHOTIC | SUGGESTED THERAPEUTIC DOSAGE RANGE (mg/kg body weight |
|---|---|
| Chlopromazine (Thorazine) | 100–1000 |
| Thioridazine (Mellaril) | 100–800 |
| Mesoridazine (Lidanar, Serentil) | 50–400 |
| Piperacetazine (Quide) | 20–160 |
| Trifluoperazine (Stelazine) | 5–60 |
| Perphenazine (Trilafon) | 8–64 |
| Fluphenazine (Permitil, Prolixin) | 2–20 |
| Thiothixene (Navane) | 2–120 |
| Haloperidol (Haldol) | 2–20 |
| Loxapine (Loxitane) | 20–160 |
| Molindone (Lidone, Moban) | 20–200 |
| Clozapine (Clozaril) | 25–400 |

EXAMPLES

The following examples are submitted for illustrative purposes only and should not be interpreted as limiting the invention in any way. A person of ordinary skill, with knowledge of this invention and of the prior art, will readily think of other subjects, other dysfunctions, and other glutamatergic substances that are readily substituted in the following examples. Also, the patents and publications cited in this disclosure reflect the level of skill the art to which this invention pertains, and are herein individually incorporated by reference to the extent that they supplement, explain, provide a background for or teach methodology, techniques and/or compositions employed herein. Those of skill in the art will readily appreciate that the foregoing protocol can be used, with only minor modifications, to prepare the other compounds of the present invention.

Example 1

In Vitro Physiological Testing

The physiological effects of Ampakines may be tested in vitro with slices of rat hippocampus according to the following procedure. Excitatory responses (field EPSPs) are measured in hippocampal slices, which are maintained in a recording chamber continuously perfused with artificial cerebrospinal fluid (ACSF). During a 15–30 minute interval, the perfusion medium is switched to one containing various concentrations of the test compounds. Responses collected immediately before and at the end of drug perfusion were superimposed in order to calculate both the percent increase in EPSP amplitude and percent increase in the width of the response at one-half the peak height (half-width).

To conduct these tests, the hippocampus was removed from anesthetized, 2 month old Sprague-Dawley rats and in vitro slices (400 micrometers thick) were prepared and maintained in an interface chamber at 35° C. using conventional techniques [see, for example, Dunwiddie and Lynch, *J. Physiol.* 276: 353–367 (1978)]. The chamber was constantly perfused at 0.5 mL/min with ACSF containing (in mM): NaCl 124, KCl 3, $KH_2PO_4$ 1.25, $MgSO_4$ 2.5, $CaCl_2$ 3.4, $NaHCO_3$ 26, glucose 10 and L-ascorbate 2. A bipolar nichrome stimulating electrode was positioned in the dendritic layer (stratum radiatum) of the hippocampal field CA1 close to the border of field CA3.

Current pulses (0.1 msec) through the stimulating electrode activate a population of the Schaffer-commissural (SC) fibers which arise from neurons in the field CA3 and terminate in synapses on the dendrites of CA1 neurons.

Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field excitatory post-synaptic potential or field "EPSP") which is recorded by a high impedance recording electrode positioned in the middle of the stratum radiatum of CA1.

For experiments designed to test the ability of compounds to enhance AMPA receptor currents, the intensity of the stimulation current was adjusted to produce half-maximal EPSPs (typically about 1.5–2.0 mV). Paired stimulation pulses were given every 40 sec with an interpulse interval of 200 msec (see below). The field EPSPs of the second response were digitized and analyzed to determine amplitude, half-width, and response area. If the responses were stable for 15–30 minutes (baseline), test compounds were added to the perfusion lines for a period of about 15 minutes. The perfusion was then changed back to regular ACSF.

Paired-pulse stimulation was used because stimulation of the SC fibers, in part, activates interneurons which generate an nhibitory postsynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon is employed to advantage to eliminate IPSP by delivering paired pulses separated by 200 milliseconds and using the second ("primed") response for data analysis.

The field EPSP recorded in field CA1 after stimulation of CA3 axons is known to be mediated by AMPA receptors: the receptors are present in the synapses [Kessler et al., *Brain Res.* 560: 337–341 (1991)] and drugs that selectively block the receptor selectively block the field EPSP [Muller et al., *Science*, supra]. Aniracetam increases the mean open time of the AMPA receptor channel and, as expected from this, increases the amplitude of the synaptic current and prolongs its duration [Tang et al. *Science*, supra]. These effects are mirrored in the field EPSP, as reported in the literature [see, for example, Staubli et al., Psychobiology, supra; Xiao et al., *Hippocampus* supra; Staubli et al., *Hippocampus* 2: 49–58 (1992)]. Similar results have been reported for the previously disclosed stable benzamide derivatives of aniracetam [International Patent Application Publication No. WO 94/02475 (PCT/US93/06916) (Lynch and Rogers, Regents of the University of California)].

The characteristic of a compound to produce an increase in the EPSP response has been a reliable predictor of the ability to improve memory in the 8-arm radial maze task. Furthermore, a reliable increase in the amplitude, but not the half-width, of the EPSP response is the hallmark of a compound that is efficacious in animal models of schizophrenia. As a nonlimiting example, the $EC_{50}$ values for the actions of CX516 and CX691 to increase the amplitude of the field EPSP are 180 $\mu$M and 3 $\mu$M, respectively. The increased potency in the in vitro slice model is mirrored in the comparative efficacies to reverse the effects of methamphetamine in an animal model of schizophrenia, as discussed below.

Example 2

Synergy Between an Allosteric Potentiator of AMPA Receptors and Clozapine in an Animal Model of Schizophrenia Amphetamine induction of stereotypic behavior is a well-known and widely used animal model of schizophrenia. The logic for this has been based primarily on two related sets of findings:

1) Amphetamine abuse in humans is known to provoke psychotic symptoms including paranoid ideation, delusions, hallucinations, and stereotyped compulsive behaviors; and, 2) Antipsychotic drugs that are effective in the treatment of human schizophrenia are also known to attenuate stereotypic behaviors induced in rats by amphetamines.

Finding no. (2) indicates that amphetamine-induced stereotypic behaviors in rats are a useful model for screening potential anti-schizophrenic drugs. Both findings have been instrumental in validating the hypothesis that psychotic symptoms are due, in part, to hyperactive dopaminergic transmission since amphetamines enhance dopamine release and typical neuroleptic drugs are potent dopamine receptor antagonists. The experiments described below used enhanced locomotor and stereotypic rearing activity induced by amphetamines in rats as a model. Published authority for the use and reliability of this model is found in: Janssen, et al., "Is it possible to predict the clinical effects of neuroleptic drugs (major tranquilizers) from animal data? IV. An improved experimental design for measuring the inhibitory effects of neuroleptic drugs on amphetamine- or apomorphine-induced 'Cheroing' and 'agitation' in rats" *Arzneimittel-Forschung* 17:841–854 (1967); Bentall, A. C. C. et al., "Blockade of amphetamine-induced locomotor activity and stereotypy in rats by spiroperidol but not by an atypical neuroleptic, thioridazine," *Neuropharmacology* 19:699–703 (1980); Niemegeers, C. J. E., et al., "A systematic study of the pharmacological activities of dopamine antagonists," *Life Science* 24:2201–2216 (1979); and Hornykiewicz, O., "Psychopharmacological implications of dopamine and dopamine antagonists: a critical evaluation of current evidence," *Neuroscience* 3:773–783 (1978).

In the present experiments, male Sprague-Dawley rats (250–300 g; Charles River Laboratories) were given ad libitum food and water and maintained on a 12:12 hr light:dark cycle with lights on at 6:00 AM. Behavioral studies utilized a computerized Photobeam Activity System (San Diego Instruments, San Diego, Calif.), in which each of ten test cages (standard polycarbonate animal cage; 26 cm×48 cm×20 cm; W×L×H) were surrounded by two photobeam arrays that were placed to detect locomotor behavior with a lower array and rearing behavior with an upper array. Locomotor and rearing activities were continuously monitored by computer for all ten test cages. Test cages (with photobeam arrays) were placed in a partially darkened room with room ventilation as background noise. On the test day, naive rats were initially placed in the test cages and baseline behavioral activity in the novel environment was monitored during a 30-minute acclimation period. The rats were then injected (i.p.) with vehicle or drug(s) dissolved in vehicle and immediately returned to the test cage and monitored undisturbed for 90 minutes.

Experimental groups (n=10–12, except vehicle, n=6) were 1) vehicle (saline or 1% lactic acid, pH 5.0); 2) S-(+)-methamphetamine HCl (METH; 2.0 mg/kg); 3) METH (2 mg/kg)+CX516 (10 mg/kg); 4) METH (2 mg/kg)+clozapine (1.0 mg/kg); and 5) METH (2 mg/kg)+CX516 (10 mg/kg)+clozapine (1.0 mg/kg). Behavioral experiments were repeated at least twice for each condition. Photobeam breaks were summed by the computer into ten-minute periods for analysis. Group means and standard errors are reported in the figures; means and standard deviations were used for statistical analysis by unpaired, two-tailed t test assuming unequal variance.

Figure 2:
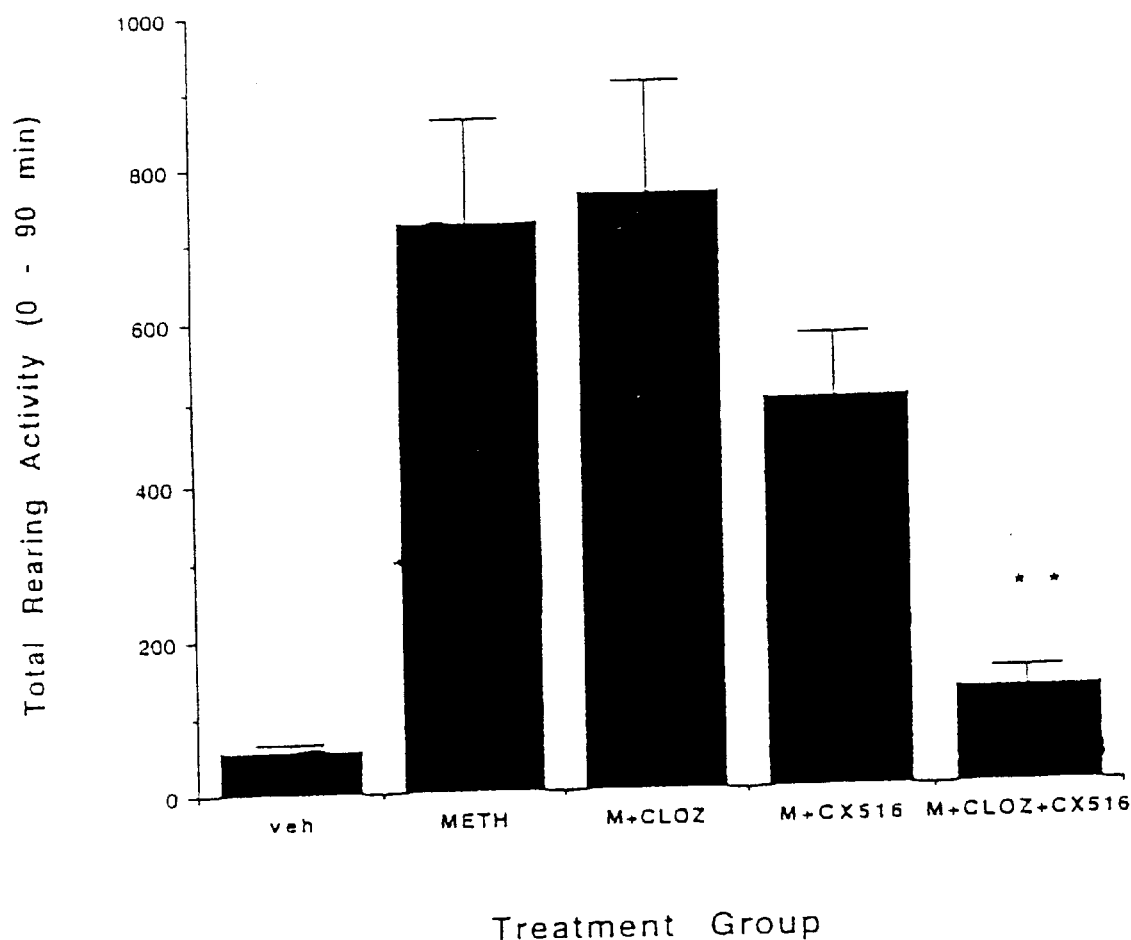

Activity measurements presented in FIGS. 1 and 2 show that CX516 synergistically enhanced the antagonistic activity of clozapine (1.0 mg/kg), a commonly-used atypical antipsychotic, in the methamphetamine animal model described above. Clozapine (1.0 mg/kg) alone had no effect (−5%) on METH-induced rearing activity, whereas CX516 (10 mg/kg) caused a modest (34%), but statistically insignificant, antagonism of METH-induced stereotypic rearing. However, together, the combination of clozapine and CX516 acted synergistically and greatly reduced METH-induced rearing activity during the 90-minute test period. After correction for the rearing activity of vehicle-treated control rats, the clozapine/CX516 combination reduced METH rearing activity by 90%.

In an additional experiment, the combination of CX516 (10 mg/kg) and another atypical antipsychotic, risperidone (0.1 mg/kg), appeared to be synergistic by completely reducing METH-induced rearing to the vehicle level (100% reduction), whereas each agent alone reduced rearing by 28% and 51%, respectively. ($p<0.01$ vs METH+RISP)(see Table 1 for a tabular compilation of representative synergistic interactions between Ampakines and antipsychotics).

Example 3

Figure 3:
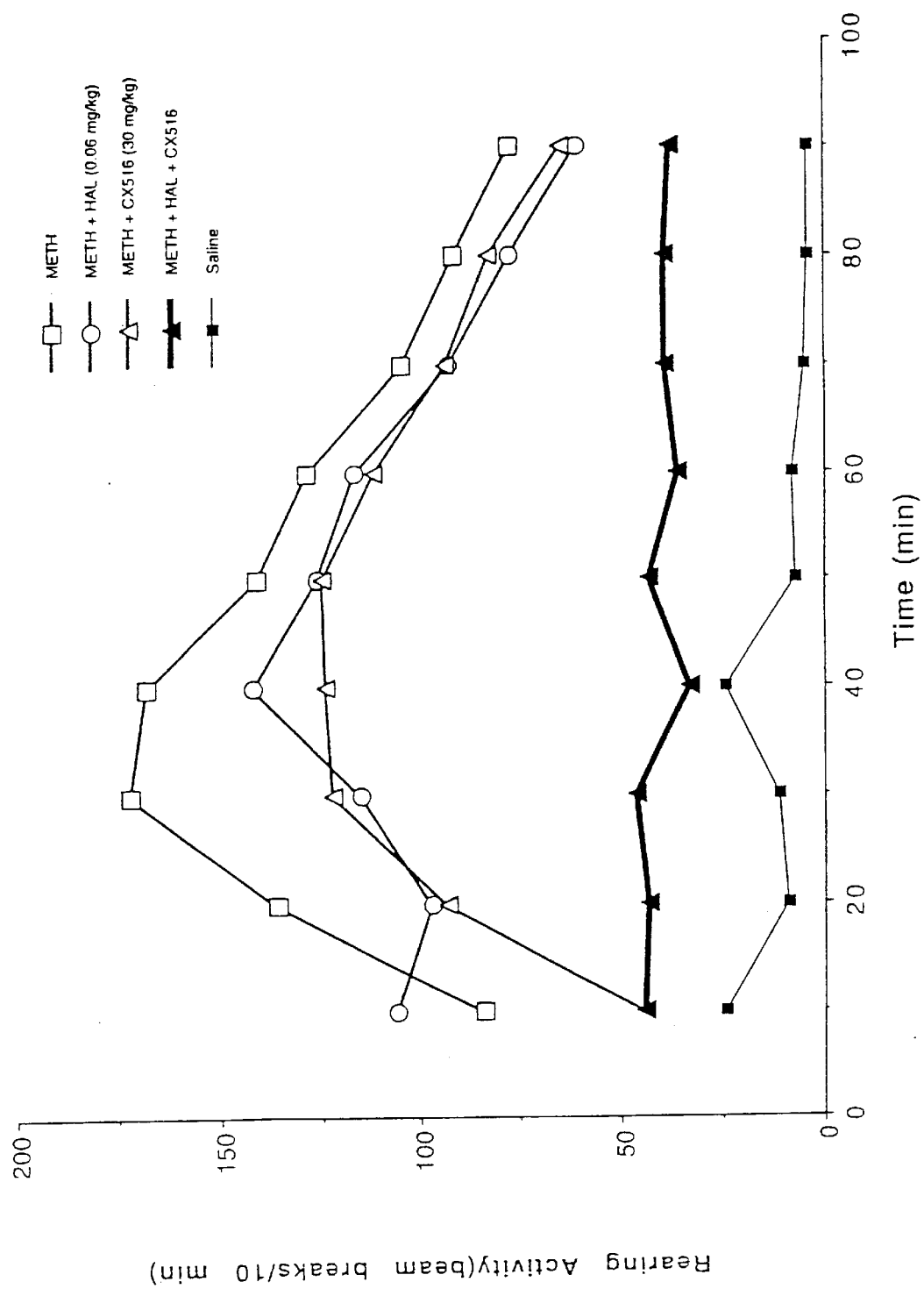
FIGS. 3 and 4 show that a representative Ampakine (CX516) synergistically enhances haloperidol antagonism of methamphetamine-induced stereotypic rearing activity.
Figure 4:
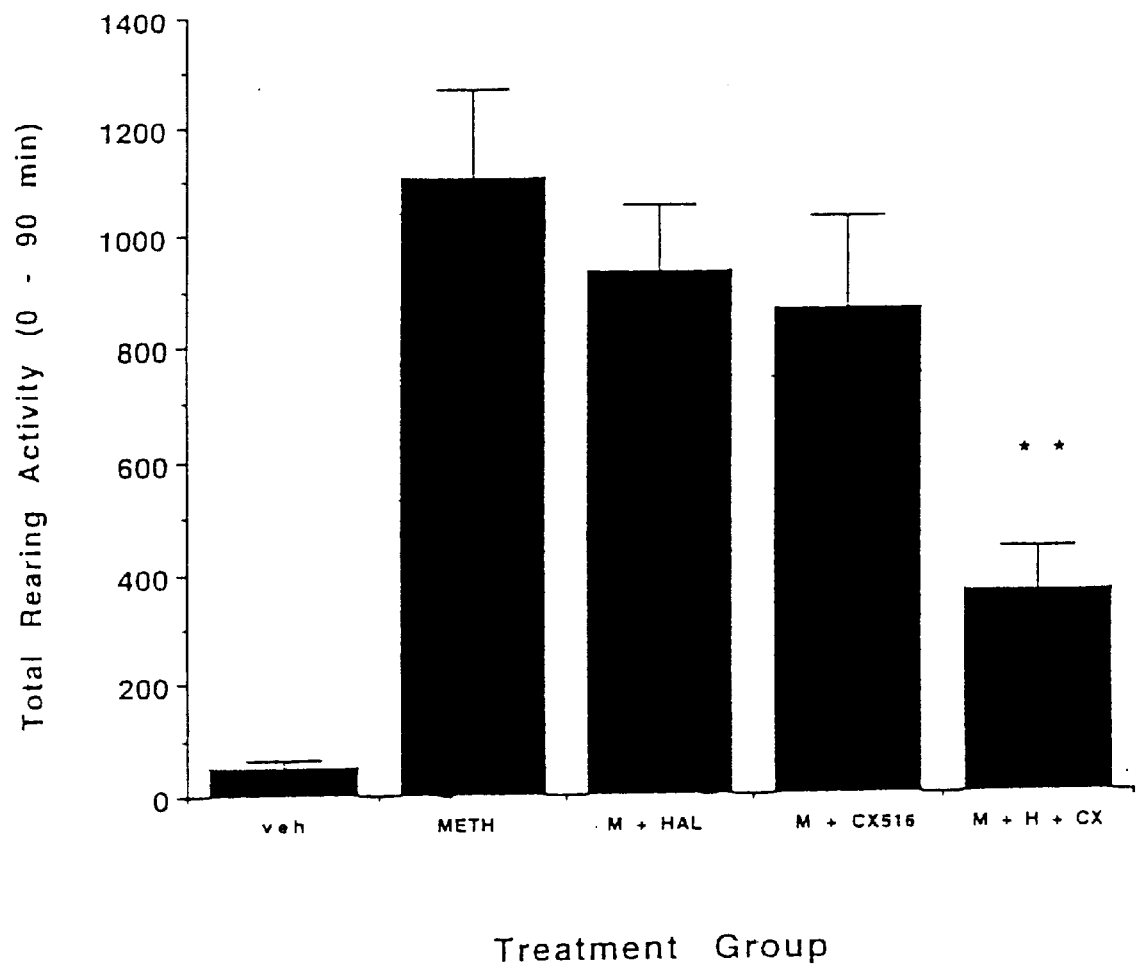

Synergy between an Ampakine and Haloperidol in the Methamphetamine Hyperactivity Animal Model of Schizophrenia Using the same methods described in the previous example, the test drug was combined with the commonly-used typical neuroleptic, haloperidol. As shown in FIGS. 3 and 4, haloperidol (0.06 mg/kg) or CX516 (30 mg/kg) each produced modest, non-significant antagonism of METH-induced stereotypic rearing activity of 15% and 22%, respectively. However, the combination of the same doses of haloperidol and CX516 was synergistic, reducing METH-induced rearing activity more completely than the sum of the effects of either drug alone: 67% vs 37%. Analysis of the difference between the effect of the haloperidol/CX516 combination and haloperidol alone by two-tailed, unpaired t test was highly significant ($p<0.0005$). This same dose combination also produced a synergistic effect when locomotor activity (LMA) was measured: 9% or 10% reduction of METH LMA for haloperidol (0.06 mg/kg) or CX516 (30 mg/kg), respectively, whereas the drug combination reduced METH LMA by 56% ($p<0.005$ vs METH+HAL 0.06 mg/kg).

TABLE 1

Percent Reduction in Methamphetamine Induced Activity

| Antipsychotic (dose in mg/kg) | Activity | Antipsychotic alone | CX516 alone | CX516 plus Antipsychotic |
|---|---|---|---|---|
| Haloperidol (0.06)[1] | Rearing | 16 | 23 | 71 |
| | Crossing | 9 | 10 | 60 |
| Haloperidol (0.12) | Rearing | 69 | 43 | 84 |
| | Crossing | 66 | 43 | 76 |
| Fluphenazine (0.2) | Rearing | 57 | 37 | 81 |
| | Crossing | 54 | 47 | 79 |
| Clozapine (1) | Rearing | −5 | 34 | 90 |
| | Crossing | −6 | −32 | 35 |
| Risperidone (0.1) | Rearing | 51 | 28 | 102 |
| | Crossing | 43 | 0 | 54 |

[1]The dose of CX516 was 10 mg/kg in all experiments except 30 mg/kg in this case.

Example 4

Receptor Interactions

The classic typical antipsychotics, such as haloperidol, chlorpromazine and fluphenazine, all have in common the ability to potently antagonize the D2 dopamine receptor and block dopaminergic transmission. Early studies correlated the clinical efficacy of typical antipsychotics with their potency as dopamine receptor antagonists, giving rise to the dopamine hypothesis of schizophrenia: e.g., Creese et al., *Science* 192:481–482, (1976). Newer atypical antipsychotics, such as clozapine, risperidone and olanzapine generally are potent antagonists at serotonin receptors, but may still be relatively potent antagonists at dopamine receptors.

On the other hand, Ampakines, typified here by CX516 and CX691, are quite specific for AMPA-type glutamate receptors. Table 2 presents the results of radioligand binding studies that show a lack of interaction between Ampakines and dopaminergic or serotonergic receptors. Thus, one skilled in the art would not expect that either additive or synergistic effects would result upon co-administration of an Ampakine with a typical or atypical antipsychotic.

TABLE 2

Radioligand Binding Analysis of Potential Interactions between Select Ampakines and Select Neurotransmitter Receptors

| Neurotransmitter | Radioligand | Ampakine | Concentration (Molar) | % Inhibition of ligand binding |
|---|---|---|---|---|
| Adrenergic | [$^3$H]-Prazosin | CX516 | 1E-5 | −0.2 |
| | | | 1E-7 | −3.5 |
| | | | 1E-9 | 0.0 |
| Dopaminergic | [$^3$H]-Spiperone | CX516 | 1E-5 | −2.8 |
| | | | 1E-7 | 0.6 |
| | | | 1E-9 | −5.1 |
| Muscarinic | [$^3$H]-QNB | CX516 | 1E-5 | 5.3 |
| | | | 1E-7 | 0.4 |
| | | | 1E-9 | 5.5 |
| Serotoninergic | [$^3$H]-dLSD | CX516 | 1E-5 | 9.1 |
| | | | 1E-7 | 9.9 |
| | | | 1E-9 | 5.5 |
| Adrenergic | [$^3$H]-Prazosin | CX691 | 1E-4 | 7.0 |
| | | | 1E-7 | −7.5 |
| Dopamine | [$^3$H]-Spiperone | CX691 | 1E-4 | 10.7 |
| | | | 1E-7 | 6.1 |
| Muscarinic | [$^3$H]-QNB | CX691 | 1E-4 | −3.7 |
| | | | 1E-7 | −8.0 |
| Serotonin | [$^3$H]-dLSD | CX691 | 1E-4 | 27.0 |
| | | | 1E-7 | 1.6 |

Example 5

Administration to Humans

A first step in treating humans is generally determining that a particular patient exhibits the symptoms of a psychotic behaviour such as Schizophrenia or Schizophreniform Disorder or Schizoaffective Disorder or Delusional Disorder or Brief Psychotic Disorder or Psychotic Disorder Due to a General Medical Condition or Psychotic Disorder Not Otherwise Specified. This determination is made by a person skilled in the art using a number of readily available diagnostic procedures. In general, the presence of typical DSMIV psychotic dysfunctions in humans can be ascertained via observation, diagnosis, family history, questionnaires or interviews. The success of treatment is measured by monitoring and recording the abatement of the symptoms of the treated behavioral disorder.

In addition, the present invention provides for kits with unit doses of AMPA up-modulating drugs and neuroleptics either in oral or injectable doses. In addition to the containers containing the unit doses will be a informational package insert describing the use and attendant benefits of the drugs in treating neurodegenerative pathologies not significantly affecting memory or learning. Preferred compounds and unit doses include those described herein above.

We claim:

1. A method for treating schizophrenia in a subject, said method comprising administering an effective amount of a composition that comprises a first compound that enhances the stimulation of α-amino-3-hydroxy-5-methyl-isoxazole-4-propionic acid ("AMPA") receptors in said subject and a second antipsychotic compound.

2. The method of claim 1 wherein the composition is administered orally.

3. The method of claim 1 wherein the composition is administered by injection.

4. A kit, comprising a container containing the composition of claim 1 and instructions for using the composition for treating schizophrenia in a subject.

5. A method in accordance with claim 1 wherein said first compound has the following formula, with ring vertices numbered as shown:

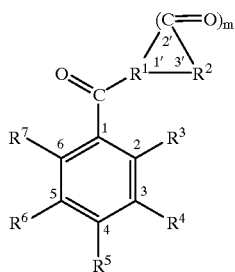

in which:

$R^1$ is a member selected from the group consisting of N and CH;

m is 0 or 1;

$R^2$ is a member selected from the group consisting of $(CR^8_2)_{n-m}$ and $C_{n-m}R^8_{2(n-m)-2}$, in which n is 4, 5, 6, or 7, the $R^8$'s in any single compound being the same or different, each $R^8$ being a member selected from the group consisting of H and $C_1$–$C_6$ alkyl, or one $R^8$ being combined with either $R^3$ or $R^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of $CH_2$, $CH_2$—$CH_2$, CH=CH, O, NH, N($C_1$–$C_6$ alkyl), N=CH, N=C($C_1$–$C_6$ alkyl), C(O), O—C(O), C(O)—O, CH(OH), NH—C(O), and N($C_1$–$C_6$ alkyl)—C(O);

$R^3$, when not combined with any $R^8$, is a member selected from the group consisting of H, $C_1$–$C_6$ alkyl, and $C_1$–$C_6$ alkoxy;

$R^4$ is either combined with $R^5$ or is a member selected from the group consisting of H, OH, and $C_1$–$C_6$ alkoxy;

$R^5$ is either combined with $R^4$ or is a member selected from the group consisting of H, OH, $C_1$–$C_6$ alkoxy, amino, mono($C_1$–$C_6$ alkyl)amino, di($C_1$–$C_6$ alkyl) amino, and $CH_2OR^9$, in which $R^9$ is a member selected from the group consisting of H, $C_1$–$C_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of $C_1$–$C_3$ alkyl, $C_1$–$C_3$ alkoxy, hydroxy, halo, amino, alkylamino, dialkylamino, and methylenedioxy;

$R^6$ is either H or $CH_2OR^9$;

$R^4$ and $R^5$ when combined form a member selected from the group consisting of

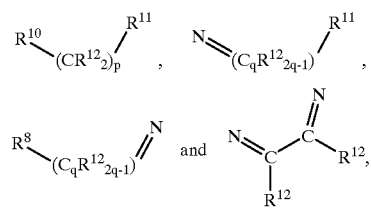

in which $R^{10}$ is a member selected from the group consisting of O, NH and N($C_1$–$C_6$ alkyl);

$R^{11}$ is a member selected from the group consisting of O, NH and N($C_1$–$C_6$ alkyl);

$R^{12}$ is a member selected from the group consisting of H and $C_1$–$C_6$ alkyl, and when two or more $R^{12}$'s are present in a single compound, such $R^{12}$'s are the same or different;

p is 1, 2, or 3; and q is 1 or 2; and $R^7$, when not combined with any $R^8$, is a member selected from the group consisting of H, $C_1$–$C_6$ alkyl, and $C_1$–$C_6$ alkoxy.

6. A method in accordance with claim 5 in which $R^2$ is a member selected from the group consisting of $(CHR^8)_{n-m}$ and $C_{n-m}HR^8_{2(n-m)-3}$, and $R^3$ is a member selected from the group consisting of H, $C_1$–$C_6$ alkyl, and $C_1$–$C_6$ alkoxy.

7. A method in accordance with claim 5 in which $R^2$ is a member selected from the group consisting of $(CHR^8)_{n-m}$ and $C_{n-m}HR^8_{2(n-m)-3}$, and one $R^8$ is combined with either $R^3$ or $R^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of $CH_2$, $CH_2$—$CH_2$, CH=CH, O, NH, N($C_1$–$C_6$ alkyl), N=CH, N=C($C_1$–$C_6$ alkyl), C(O), O—C(O), C(O)—O, CH(OH), NH—C(O), and N($C_1$–$C_6$ alkyl)—C(O).

8. A method in accordance with claim 5 in which $R^2$ is a member selected from the group consisting of $(CHR^8)_{n-m}$ and $C_{n-m}HR^8_{2(n-m)-3}$, and one $R^8$ is combined with either $R^3$ or $R^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of $CH_2$, $CH_2$—$CH_2$, CH—CH, O, NH, C(O), and CH(OH).

9. A method in accordance with claim 5 in which $R^2$ is a member selected from the group consisting of $(CHR^8)_{n-m}$ and $C_{n-m}HR^8_{2(n-m)-3}$, and one $R^8$ is combined with either $R^3$ or $R^7$ to form a single divalent linking moiety linking the no. 3' ring vertex to either the no. 2 or the no. 6 ring vertices, the linking moiety being a member selected from the group consisting of $CH_2$, O, NH, C(O), and CH(OH).

10. A method in accordance with claim 5 in which m is zero, $R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, NH, C(O), and CH(OH).

11. A method in accordance with claim 5 in which m is zero, $R^2$ is a member selected from the group consisting of $CHR^8—CH_2—CH_2—CH_2$ and $CHR^8—CH_2—CH_2—CH_2—CH_2$, in which $R^8$ is combined with $R^7$ to form a single divalent linking moiety linking the 2 and 3' ring vertices, the linking moiety being a member selected from the group consisting of $CH_2$, O, and NH.

12. A method in accordance with claim 5 in which $R^4$ and $R^5$ are combined to form a member selected from the group consisting of

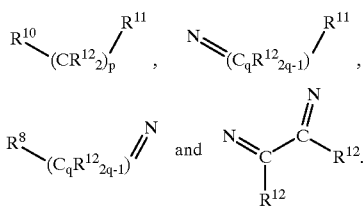

13. A method in accordance with claim 12 in which $R^{12}$ is a member selected from the group consisting of H and $CH_3$.

14. A method in accordance with claim 5 in which $R^4$ and $R^5$ are combined to form a member selected from the group consisting of

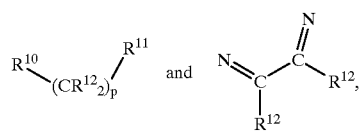

in which $R^{12}$ is a member selected from the group consisting of H and $CH_3$.

15. A method in accordance with claim 5 in which:
m is zero;
$R^2$ is a member selected from the group consisting of $CHR^8—CH_2—CH_2—CH_2$ and $CHR^8—CH_2—CH_2—CH_2—CH_2$, in which $R^8$ is combined with $R^7$ to form a single divalent linking moiety linking the 2 and 3' ring vertices, the linking moiety being a member selected from the group consisting of $CH_2$, O, NH, C(O), and CH(OH);
$R^4$ and $R^5$ are combined to form a member selected from the group consisting of

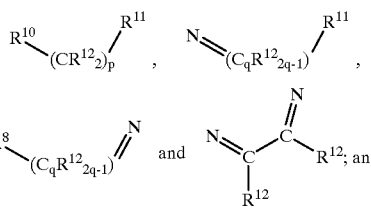

$R^{10}$ is O;
$R^{11}$ is O;
$R^{12}$ is a member selected from the group consisting of H and $CH_3$.

16. A method in accordance with claim 5 in which $R^4$ and $R^5$ are combined to form a member selected from the group consisting of

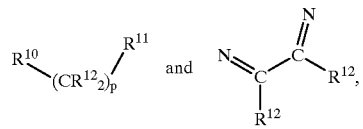

in which $R^{10}$ is O, $R^{11}$ is O, and $R^{12}$ is a member selected from the group consisting of H and $CH_3$.

17. A method in accordance with claim 5 in which:
m is zero;
$R^2$ is a member selected from the group consisting of $CHR^8—CH_2—CH_2—CH_2$ and $CHR^8—CH_2—CH_2—CH_2—CH_2$, in which R8 is combined with $R^7$ to form a single divalent linking moiety linking the 2 and 3' ring vertices, the linking moiety being a member selected from the group consisting of $CH_2$, O, and NH;
$R^4$ and $R^5$ are combined to form a member selected from the group consisting of

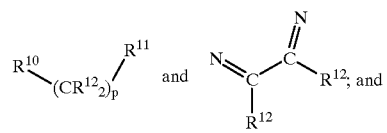

$R^{10}$ is O;
$R^{11}$ is O; and
$R^{12}$ is a member selected from the group consisting of H and $CH_3$.

18. A method in accordance with claim 5 in which:
m is zero;
$R^1$ is N;
$R^2$ is $CHR^8—CH_2—CH_2—CH_2$;
$R^3$ is H;
$R^3$ is H;
$R^4$ and $R^5$ are combined to form

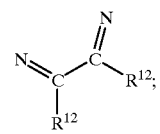

$R^6$ is H;
$R^8$ is combined with $R^7$ to form a single O atom linking the 2 and 3' ring vertices; and
$R^{12}$ is H.

19. A method in accordance with claim 1, wherein the first compound has the following structure:

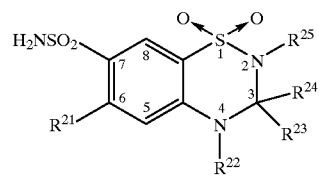

wherein
$R^{21}$ is either H, halo or $CF_3$;
$R^{22}$ and $R^{23}$ either are both H or are combined to form a double bond bridging the 3 and 4 ring vertices;

$R^{24}$ is either H, $C_1$–$C_6$ alkyl, $C_5$–$C_7$ cycloalkyl, $C_5$–$C_7$ cycloalkenyl, Ph, $CH_2Ph$, $CH_2SCH_2Ph$, $CH_2X$, $CHX_2$, $CH_2SCH_2CF_3$, $CH_2SCH_2CH=CH_2$, or

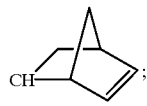

and $R^{25}$ is a member selected from the group consisting of H and $C_1$–$C_6$ alkyl.

20. A method in accordance with claim 1, wherein the first compound has the following structure:

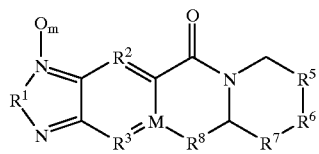

in which:
$R^1$ is oxygen or sulfur;
$R^2$ and $R^3$ are independently selected from the group consisting of —N=, —CR=, and —CX=;
M is =N or =CR$^4$—, wherein $R^4$ and $R^8$ are independently R or together form a single linking moiety linking M to the ring vertex 2', the linking moiety being selected from the group consisting of a single bond, —CR$_2$—, —CR=CR—, —C(O)—, —O—, —S(O)$_y$—, —NR—, and —N=;
$R^5$ and $R^7$ are independently selected from the group consisting of —(C$_2$)$_n$—, —C(O)—, —CR=CR—, —CR=CX—, —C(RX)—, —CX$_2$—, —S—, and —O—; and
$R^6$ is selected from the group consisting of —(CR$_2$)$_m$—, —C(O)—, —CR=CR—, —C(RX)—, —CR$_2$—, —S—, and —O—;
wherein
X is —Br, —Cl, —F, —CN, —NO$_2$, —OR, —SR, —NR$_2$, —C(O)R—, —CO$_2$R, or —CONR$_2$; and
R is hydrogen, $C_1$–$C_6$ branched or unbranched alkyl, which may be unsubstituted or substituted with one or more functionalities defined above as X, or aryl, which may be unsubstituted or substituted with one or more functionalities defined above as X;
m and p are independently 0 or 1;
n and y are independently 0, 1 or 2.

21. The method of claim I wherein the second antipsychotic compound is selected from the group consisting of typical and atypical antipsychotic compounds.

22. The method of claim 21 wherein the typical antipsychotic compound is selected from the group consisting of haloperidol, chlorpromazine, fluphenazine, perphenazine, molindone, pimozide, trifluoperazine and thioridazine.

23. The method of claim 21 wherein the atypical antipsychotic compound is selected from the group consisting of clozapine, risperidone, olanzapine, sertindole, M100907, ziprasidone, seroquel, zotepine, amisulpride, and iloperidone.

24. The method of claim 1 wherein the second antipsychotic compound is administered at subtherapeutic levels.

25. A method in accordance with claim 5, wherein the first compound has the following structure:

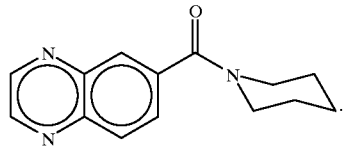

26. A method in accordance with claim 20 in which the first compound is selected from the group consisting of the following compounds:

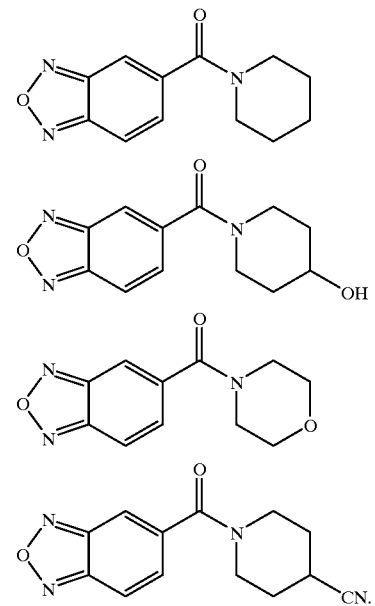

* * * * *